US008703972B2

(12) United States Patent
Ding et al.

(10) Patent No.: US 8,703,972 B2
(45) Date of Patent: Apr. 22, 2014

(54) CATALYST SYSTEMS AND POLYMER RESINS HAVING IMPROVED BARRIER PROPERTIES

(71) Applicant: Chevron Phillips Chemical Company LP, The Woodlands, TX (US)

(72) Inventors: Errun Ding, Bartlesville, OK (US); Albert P. Masino, Tulsa, OK (US); Joel L. Martin, Bartlesville, OK (US); Youlu Yu, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 13/860,604

(22) Filed: Apr. 11, 2013

(65) Prior Publication Data
US 2013/0225820 A1 Aug. 29, 2013

Related U.S. Application Data

(62) Division of application No. 12/890,455, filed on Sep. 24, 2010, now Pat. No. 8,501,651.

(51) Int. Cl.
*C07F 11/00* (2006.01)
(52) U.S. Cl.
USPC .............................. 549/206; 546/2
(58) Field of Classification Search
USPC .............................. 549/206; 546/2
See application file for complete search history.

(56) References Cited

U.S. PATENT DOCUMENTS

| | | | |
|---|---|---|---|
| 3,248,179 A | 4/1966 | Norwood | |
| 4,060,480 A | 11/1977 | Reed et al. | |
| 4,452,910 A | 6/1984 | Hopkins et al. | |
| 4,501,885 A | 2/1985 | Sherk et al. | |
| 4,588,790 A | 5/1986 | Jenkins, III et al. | |
| 4,794,096 A | 12/1988 | Ewen | |
| 5,352,749 A | 10/1994 | DeChellis et al. | |
| 5,376,611 A | 12/1994 | Shveima | |
| 5,418,200 A | 5/1995 | Carney et al. | |
| 5,436,304 A | 7/1995 | Griffin et al. | |
| 5,455,314 A | 10/1995 | Burns et al. | |
| 5,565,175 A | 10/1996 | Hottovy et al. | |
| 5,575,979 A | 11/1996 | Hanson | |
| 5,684,100 A | 11/1997 | Carney et al. | |
| 5,919,983 A | 7/1999 | Rosen et al. | |
| 5,942,462 A | 8/1999 | Mitchell et al. | |
| 6,107,230 A | 8/2000 | McDaniel et al. | |
| 6,165,929 A | 12/2000 | McDaniel et al. | |
| 6,239,235 B1 | 5/2001 | Hottovy et al. | |
| 6,262,191 B1 | 7/2001 | Hottovy et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,432,496 B1 | 8/2002 | Klosiewicz | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,583,241 B1 | 6/2003 | Beach et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 6,833,415 B2 | 12/2004 | Kendrick et al. | |
| 6,913,809 B2 | 7/2005 | Wolak | |
| 6,914,113 B2 | 7/2005 | McLeod et al. | |
| 6,984,698 B2 | 1/2006 | McLeod et al. | |
| 7,163,906 B2 | 1/2007 | McDaniel et al. | |
| 7,176,259 B1 | 2/2007 | Klosiewicz | |
| 7,214,642 B2 | 5/2007 | McDaniel et al. | |
| 7,226,886 B2 | 6/2007 | Jayaratne et al. | |
| 7,294,599 B2 | 11/2007 | Jensen et al. | |
| 7,501,372 B2 | 3/2009 | Thorn et al. | |
| 7,541,481 B2 | 6/2009 | Mihan et al. | |
| 7,601,655 B2 | 10/2009 | Katsin | |
| 7,732,542 B2 | 6/2010 | Yang et al. | |
| 7,884,163 B2 | 2/2011 | McDaniel et al. | |
| 7,884,165 B2 | 2/2011 | McDaniel et al. | |
| 8,501,651 B2 | 8/2013 | Ding et al. | |
| 2007/0007680 A1 | 1/2007 | Barre et al. | |
| 2008/0118749 A1 | 5/2008 | Aubee et al. | |
| 2009/0035545 A1 | 2/2009 | Guenther et al. | |
| 2012/0077008 A1 | 3/2012 | St. Jean et al. | |

FOREIGN PATENT DOCUMENTS

| | | |
|---|---|---|
| EP | 0509294 A2 | 10/1992 |
| EP | 0620830 A1 | 10/1994 |
| WO | 9411410 A1 | 5/1994 |
| WO | 9623006 | 8/1996 |

(Continued)

OTHER PUBLICATIONS

Alathon® M6210 High Density (MMW) Polyethylene, LyondellBasell Industries, IDES Prospector, 2010, 1 page, IDES.
Benham, E. A., et al., "Mixed organo/oxide chromium polymerization catalysts," Journal of Macromolecular Science-Chemistry, 1988, vol. A25, No. 3, pp. 259-283, Marcel Dekker, Inc.

(Continued)

*Primary Examiner* — Charanjit Aulakh
(74) *Attorney, Agent, or Firm* — Rodney B. Carroll; Conley Rose, P.C.; Cheryl L. Huseman

(57) ABSTRACT

A catalyst system comprising a half-sandwich chromium complex, an activator support and an optional cocatalyst. A compound of formula Cp'Cr(Cl)$_2$(L$_n$), where Cp' is $\eta^5$-C$_5$H$_4$CH$_2$CH$_2$CH=CH$_2$ and L$_n$ is pyridine, THF or diethylether. A compound of formula Cp"Cr(Cl)$_2$(L$_n$), where Cp" is $\eta^5$-C$_5$H$_4$C(Me)$_2$CH$_2$CH$_2$CH=CH$_2$ and L$_n$ is pyridine, THF or diethylether.

28 Claims, 5 Drawing Sheets

(56) References Cited

FOREIGN PATENT DOCUMENTS

| WO | 9627621 | 9/1996 |
|----|---------|--------|
| WO | 2004020479 A2 | 3/2004 |
| WO | 2007008361 A1 | 1/2007 |
| WO | 2012040144 A1 | 3/2012 |
| WO | 2012040147 A1 | 3/2012 |

OTHER PUBLICATIONS

Bird, R. Byron, et al., "Fluid Mechanics," Dynamics of Polymeric Liquids, 1987, vol. 1, 2nd Edition, pp. xiii-xviii and 171-172, John Wiley & Sons, Inc.

Brieger, Gottfried, et al., "A new route to brex-4-ene," Journal of Organic Chemistry, 1971, vol. 36, No. 1, pp. 243-244.

Cotton, F. Albert, et al., Advanced Inorganic Chemistry, 6th Edition, 1999, cover page, title page, pp. ix-x, and publishing information, John Wiley & Sons, Inc.

Fendrick, Carol M., et al., "Transition metal organometallics and ligands," Inorganic Synthesis, 1992, vol. 29, Chapter 4, pp. 193-198, Inorganic Syntheses, Inc.

Hawley's Condensed Chemical Dictionary, 11th Edition, 1987, cover page, publishing information, content page, and pp. 862-863, Van Nostrand Reinhold Company.

Hieber, C. A., et al., "Shear-rate-dependence modeling of polymer melt viscosity," Polymer Engineering and Science, Jul. 1992, vol. 32, No. 14, pp. 931-938.

Hieber, C. A., et al., "Some correlations involving the shear viscosity of polystyrene melts," Rheologica Acta, 1989, vol. 28, pp. 321-332.

Li, Hongbo, et al., "Coordination copolymerization of severely encumbered isoalkenes with ethylene: enhanced enchainment mediated by binuclear catalysts and cocatalysts," Journal of the American Chemical Society, 2005, vol. 127, No. 42, pp. 14756-14768, American Chemical Society.

MarFlex® 9659 High Density Polyethylene, MarFlex Polyethylene, Jun. 2004, 1 page, Chevron Phillips Chemical Company LP.

MarFlex® 9659 High Density Polyethylene, Chevron Phillips Chemical Company LLC, IDES Prospector, 2010, 1 page, IDES.

McDaniel, M. P., et al., "Ethylene polymerization catalysts from supported organotransition metal complexes," Journal of Catalysis, 1989, vol. 120, pp. 170-181, Academic Press, Inc.

McDaniel, M. P., "Supported chromium catalysts for ethylene polymerization," Advances in Catalysis, 1985, vol. 33, pp. 47-98, Academic Press, Inc.

"Moisture vapor transmission rate," Wikipedia, Feb. 24, 2010, 3 pages, Wikipedia.

Noh, Seok Kyun, et al., "[Cp*(Me)Cr(.mu.-Me)]2, an electron-deficient chromium(III) alkyl with bridging methyl groups and a chromium-chromium bond," Journal of the American Chemical Society, 1989, vol. 111, No. 25, pp. 9127-9129, American Chemical Society.

Office Action dated Jan. 3, 2013 (30 pages), U.S. Appl. No. 12/890,448, filed Sep. 24, 2010.

Office Action dated Jul. 16, 2013 (10 pages), U.S. Appl. No. 12/890,448, filed Sep. 24, 2010.

Pinnavaia, Thomas J., "Intercalated clay catalysts," Science, New Series, Apr. 22, 1983, vol. 220, No. 4595, pp. 365-371, American Association for the Advancement of Science.

Product Comparison, IDES Prospector, 2010, 5 pages, IDES.

Saβmannshausen, Jörg, et al., "Half-sandwich complexes of titanium and zirconium with pendant phenyl substituents. The influence of ansa-aryl coordination on the polymerisation activity of half-sandwich catalysts," Journal of Organometallic Chemistry, 1999, vol. 592, pp. 84-94, Elsevier Science, S.A.

Shroff, R. N., et al., "Long-chain-branching index for essentially linear polyethylenes," Macromolecules, 1999, vol. 32, pp. 8454-8464, American Chemical Society.

Thomas, J. M., "Sheet silicate intercalates: new agents for unusual chemical conversions," Intercalation Chemistry, 1982, Chapter 3, pp. 55-99, Academic Press, Inc.

Derlin, Stefanie, et al., "Chain-walking olefin polymerizations with donor-substituted half-sandwich chromium complexes: Ethylene/propylene copolymer look-alikes by polymerization of propylene," XP-001515406, Macromolecules, 2008, pp. 6280-6288, vol. 41, No. 17, American Chemical Society.

Foreign communication from a related counterpart application—International Search Report and Written Opinion, PCT/US2011/052261, Feb. 21, 2012, 9 pages.

Foreign communication from a related counterpart application—International Preliminary Report on Patentability, PCT/US2011/052261, Mar. 26, 2013, 6 pages.

Foreign communication from a related counterpart application—International Search Report and Written Opinion, PCT/US2011/052266, Dec. 22, 2011, 8 pages.

Foreign communication from a related counterpart application—International Preliminary Report on Patentability, PCT/US2011/052266, Mar. 26, 2013, 5 pages.

Yan, D., et al., "Effect of long chain branching on rheological properties of metallocene polyethylene," Polymer, 1999, pp. 1737-1744, vol. 40, Elsevier Science Ltd.

CATALYST SYSTEMS AND POLYMER RESINS HAVING IMPROVED BARRIER PROPERTIES

CROSS REFERENCE TO RELATED APPLICATIONS

This application is a divisional of and claims priority to U.S. patent application Ser. No. 12/890,455 filed on Sep. 24, 2010, published as US 2012/0077665 A1, which is related to U.S. patent application Ser. No. 12/890,448 filed Sep. 24, 2010, published as US 2012/0077008 A1, both entitled "Novel Catalyst Systems and Polymer Resins Having Improved Barrier Properties," which are hereby incorporated herein by reference in their entirety for all purposes.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

The present disclosure generally relates to catalyst systems and polymer resins prepared using same. More particularly the present disclosure relates to the use of catalyst systems comprising half-sandwich chromium compounds to prepare polymer resins displaying improved barrier properties.

FIELD OF THE INVENTION

Polyolefins are plastic materials useful for making a wide variety of valued products due to their combination of stiffness, ductility, barrier properties, temperature resistance, optical properties, availability, and low cost. One of the most valued products is plastic films. In particular, PE is the one of the largest volume polymers consumed in the world. It is a versatile polymer that offers high performance relative to other polymers and alternative materials such as glass, metal, or paper. Plastic films such as PE films are mostly used in packaging applications, but they also find utility in the agricultural, medical, and engineering fields.

PE films are manufactured in a variety of grades that are usually differentiated by the polymer density, for example, low density polyethylene (LDPE), medium density polyethylene (MDPE), and high density polyethylene (HDPE), wherein each density range has a unique combination of properties making it suitable for a particular application.

Despite the many positive attributes of PE, the film product remains permeable to moisture (e.g., water) and/or gases such as oxygen and carbon dioxide. Thus, it would be desirable to develop a PE film product exhibiting improved barrier properties. It is of further interest to develop novel catalyst systems capable of producing polymer resins that can be formed into films displaying the aforementioned desirable properties.

BRIEF SUMMARY OF THE INVENTION

Disclosed herein is a catalyst system comprising a half-sandwich chromium complex, an activator support and an optional cocatalyst.

Further disclosed herein is a compound of formula Cp'Cr(Cl)$_2$(L$_n$), where Cp' is $\eta^5$-C$_5$H$_4$CH$_2$CH$_2$CH=CH$_2$ and L$_n$ is pyridine, THF or diethylether.

Also disclosed herein is a compound of formula Cp"Cr(Cl)$_2$(L$_n$), where Cp" is $\eta^5$-C$_5$H$_4$C(Me)$_2$CH$_2$CH$_2$CH=CH$_2$ and L$_n$ is pyridine, THF or diethylether.

DETAILED DESCRIPTION OF THE INVENTION

Figure 1:
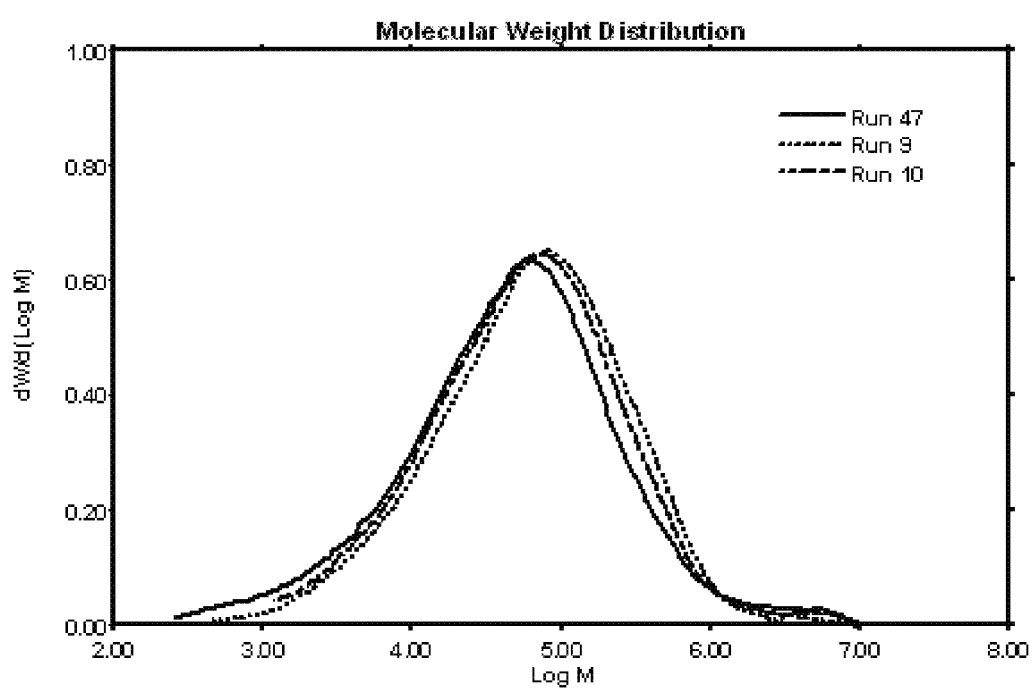
FIG. 1 is a graph of the molecular weight distribution of polymer samples from Example 1.

Disclosed herein are catalyst compositions and methods of making and using same. In an embodiment, the catalyst system comprises a transition metal complex, an activator-support, an optional additional activator and an optional cocatalyst. Such catalyst systems may be utilized in the preparation of polymer resins such as polyolefins. In an embodiment, the polymer resin comprises polyethylene, alternatively high density polyethylene. Polymer resins of the type described herein may be formed into films that display improvements in barrier properties and as such may find particular utility in food packaging applications. Hereinafter such polymer resins are termed barrier-improved polymer (BIP) compositions. In an embodiment, a BIP composition is a polyethylene homopolymer (e.g., a unimodal polyethylene homopolymer) having the physical properties and characteristics described in more detail herein.

In an embodiment, a method of preparing a BIP composition comprises contacting an alpha-olefin monomer with a catalyst system under conditions suitable for the formation of a polymer of the type described herein. Any catalyst system compatible with and able to produce polymers having the features disclosed herein may be employed. In an embodiment, the catalyst system comprises a transition-metal complex, an activator-support, and an optional cocatalyst.

The terms "catalyst composition," "catalyst mixture," "catalyst system," and the like, do not depend upon the actual product resulting from the contact or reaction of the components of the mixtures, the nature of the active catalytic site, or the fate of the cocatalyst, the transition metal complexes, any olefin monomer used to prepare a precontacted mixture, or the activator-support, after combining these components. Therefore, the terms "catalyst composition," "catalyst mixture," "catalyst system," and the like, can include both heterogeneous compositions and homogenous compositions.

With regard to the chemical groups defined herein, in one aspect, a chemical "group" can be defined or described according to how that group is formally derived from a reference or "parent" compound, for example, by the number of hydrogen atoms that are formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, an "alkenyl group" by removing one hydrogen atom from an alkene, or an alkynyl group by removing one hydrogen atom from an alkyne, while an "alkylene group" "alkenylene group" or "alkynylene group" formally can be derived by removing two hydrogen atoms from an alkane, alkene, or alkyne, respectively. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and material have three or more hydrogen atoms, as necessary for the situation, removed from an alkane. Throughout, the disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group that can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, and phosphines, and so forth. In one aspect, the hydrogen atom(s) removed to form the "organyl group," "organylene group," or "organic group" may be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" may be attached to a carbon atom not belonging to, and remote from, a functional group, for example, —CH$_2$C(O)CH$_3$, —CH$_2$NR$_2$, and the like. An "organyl group," "organylene group," or "organic group" may be aliphatic, inclusive of being cyclic or acyclic, or may be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" may be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or may be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane group, cycloalkyl, cycloalkylene, cycloalkane groups, aralkyl, aralkylene, and aralkane groups, respectively, among other groups as members.

The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or may be linear or branched unless otherwise specified. Primary, secondary, and tertiary alkyl group are derived by removal of a hydrogen atom from a primary, secondary, tertiary carbon atom, respectively, of an alkane. The n-alkyl group derived by removal of a hydrogen atom from a terminal carbon atom of a linear alkane. The groups RCH$_2$ (R≠H), R$_2$CH (R≠H), and R$_3$C (R≠H) are primary, secondary, and tertiary alkyl groups, respectively.

In an embodiment, a catalyst system for preparation of a BIP comprises the contact product of a transition metal complex, an activator-support and an optional cocatalyst. The transition metal complex may be characterized by the general formula

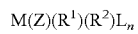

$$M(Z)(R^1)(R^2)L_n$$

wherein M is a transition metal, alternatively chromium and Z, R$^1$, and R$^2$ are ligands coordinated to M, and L$_n$ is a neutral donor group where n is 0, 1 or 2. In another embodiment L$_n$ can be THF, acetonitrile, pyridine, diethylether or bipyridine. In an embodiment, Z comprises a η$^3$ to η$^5$-cycloalkadienyl moiety. Nonlimiting examples of η$^3$ to η$^5$-cycloalkadienyl moieties suitable for use in this disclosure include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this disclosure comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like. In an embodiment, Z comprises a cyclopentadienyl moiety and the transition metal complex is termed a "half-sandwich complex." The cyclopentadienyl moiety may be characterized by the general structure;

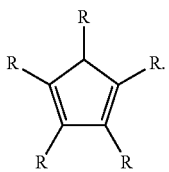

In an embodiment, each R of the cyclopentadienyl moiety can be different. In some embodiments, each R can be the same. In an embodiment, each R may be independently selected from the group consisting of hydrogen, an organyl group; or alternatively, a hydrogen and a hydrocarbyl group. In embodiments, each R can independently be H or a $C_1$ to $C_{20}$ organyl group; alternatively, H or a $C_1$ to $C_{10}$ organyl group; or alternatively, H or a $C_1$ to $C_5$ organyl group. In other embodiments, each R can independently be H or a $C_1$ to $C_{20}$ hydrocarbyl group; alternatively, H or a $C_1$ to $C_{10}$ hydrocarbyl group; or alternatively, H or a $C_1$ to $C_5$ hydrocarbyl group or alternatively H. In an embodiment, R may be a $C_1$ to $C_{60}$ organylene group; alternatively, a $C_1$ to $C_{50}$ organylene group; alternatively, $C_1$ to $C_{40}$ organylene group; alternatively, a $C_1$ to $C_{30}$ organylene group; or alternatively, a $C_1$ to $C_{20}$ organylene group. In other embodiments, each R can independently be a $C_1$ to $C_{60}$ hydrocarbylene group; alternatively, a $C_1$ to $C_{50}$ hydrocarbylene group; alternatively, a $C_1$ to $C_{40}$ hydrocarbylene group; alternatively, a $C_1$ to $C_{30}$ hydrocarbylene group; alternatively, a $C_1$ to $C_{20}$ hydrocarbylene group.

In some embodiments, each non-hydrogen R group may independently be an alkyl group. In an embodiment, the alkyl group which may be utilized as a non-hydrogen R group may be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, the alkyl group which may be utilized as a non-hydrogen R group may be a methyl group, an ethyl group, a n-propyl group, an iso-propyl group, a n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

In an embodiment, each R may independently be an alkylene group alternatively, an alkenylene group. For example, each R may independently be a methylene group, an ethylene group, a propylene group, a butylene group, a pentylene group, a hexylene group, a heptylene group, an octylene group, a nonylene group, a decylene group, a undecylene group, a dodecylene group, a tridecylene group, a tetradecylene group, a pentadecylene group, a hexadecylene group, a heptadecylene group, an octadecylene group, or a nonadecylene group; or alternatively, a methylene group, an ethylene group, a propylene group, a butylene group, a pentylene group, a hexylene group, a heptylene group, an octylene group, a nonylene group, a decylene group. In some embodiments, each R may independently be a methylene group, an ethylene group, a propylene group, a butylene group, or a pentylene group. In other embodiments, each R may independently be a methylene group; alternatively, an ethylene group; alternatively, a propylene group; alternatively, a butylene group; alternatively, a pentylene group; alternatively, a hexylene group; alternatively, a heptylene group; alternatively, an octylene group; alternatively, a nonylene group; alternatively, a decylene group; alternatively, a undecylene group; alternatively, a dodecylene group; alternatively, a tridecylene group; alternatively, a tetradecylene group; alternatively, a pentadecylene group; alternatively, a hexadecylene group; alternatively, a heptadecylene group; alternatively, an octadecylene group; or alternatively, a nonadecylene group. In some embodiments, each R may independently be a eth-1,2-ylene group, a prop-1,3-ylene group, a but-1,4-ylene group, a but-2,3-ylene group, a pent-1,5-ylene group, a 2,2-dimethylprop-1,3-ylene group, a hex-1,6-ylene group, or a 2,3-dimethylbut-2,3-ylene group; alternatively, eth-1,2-ylene group, a prop-1,3-ylene group, a but-1,4-ylene group, a pent-1,5-ylene group, or a hex-1,6-ylene group; alternatively, a eth-1,2-ylene group; alternatively, a prop-1,3-ylene group; alternatively, a but-1,4-ylene group; alternatively, a but-2,3-ylene group; alternatively, a pent-1,5-ylene group; alternatively, a 2,2-dimethyl-prop-1,3-ylene group; alternatively, a hex-1,6-ylene group; or alternatively, a 2,3-dimethylbut-2,3-ylene group.

In an embodiment, each R may independently be an ethenylene group, a propenylene group, a butenylene group, a pentenylene group, a hexenylene group, a heptenylene group, an octenylene group, a nonenylene group, a decenylene group, a undecenylene group, a dodecenylene group, a tridecenylene group, a tetradecenylene group, a pentadecenylene group, a hexadecenylene group, a heptadecenylene group, an octadecenylene group, or a nonadecenylene group; or alternatively, an ethenylene group, a propenylene group, a butenylene group, a pentenylene group, a hexenylene group, a heptenylene group, an octenylene group, a nonenylene group, a decenylene group. In some embodiments, each R may independently be an ethenylene group, a propenylene group, a butenylene group, or a pentenylene group. In other embodiments, each R may independently be an ethenylene group; alternatively, a propenylene group; alternatively, a butenylene group; alternatively, a pentenylene group; alternatively, a hexenylene group; alternatively, a heptenylene group; alternatively, an octenylene group; alternatively, a nonenylene group; alternatively, a decenylene group; alternatively, a undecenylene group; alternatively, a dodecenylene group; alternatively, a tridecenylene group; alternatively, a tetradecenylene group; alternatively, a pentadecenylene group; alternatively, a hexadecenylene group; alternatively, a heptadecenylene group; alternatively, an octadecenylene group; or alternatively, a nonadecenylene group. Generally, the carbon-carbon double bond(s) of any alkenylene group disclosed herein may be located at any position within the alkenylene group. In an embodiment, the alkenylene group contains a terminal carbon-carbon double bond.

In an embodiment, each R of the cyclopentadienyl group comprises an alkyl group, alternatively a methyl group. In an embodiment, Z comprises a pentamethylcyclopentadienyl group, hereinafter designated Cp*. In another embodiment, at least one R of the cyclopentadienyl group comprises an organylene group, alternatively a hydrocarbylene group. In an embodiment the cyclopentadienyl group comprises one R group comprising —$C(CH_3)_2CH_2CH_2CH=CH_2$ and the remaining R groups comprise hydrogen, hereinafter designated Cp'. Alternatively the cyclopentadienyl group comprises one R group comprising —$CH_2CH_2CH=CH_2$ and the remaining R groups comprise hydrogen and is hereinafter designated Cp''. Cp' and Cp'' may be prepared using any suitable methodology. For example, suitable preparation methodologies are described in Brieger, et al., J. Org. Chem. 36 (1971) p 243; Bochmann, et al., in J. Organmet. Chem. 592 (1999); Theopold, et al., J. Am. Chem. Soc. 111 (1989) p 9127; and Fendrick, et al., in Inorg. Synth., 29 (1992) p 193, each of which are incorporated by reference herein in its entirety.

In an embodiment $R^1$ and $R^2$ can be different. In other embodiments, $R^1$ and $R^2$ can be the same. In an embodiment, each of $R^1$ and $R^2$ may be independently selected from the group consisting of a halide, an organyl group, or, a hydrocarbyl group. In embodiments, each of $R^1$ and $R^2$ can independently be a halide, a $C_1$ to $C_{20}$ organyl group; alternatively, a $C_1$ to $C_{10}$ organyl group; or alternatively, a $C_1$ to $C_5$ organyl group. In other embodiments, each of $R^1$ and $R^2$ can independently be a halide, a $C_1$ to $C_{20}$ hydrocarbyl group; alternatively, a $C_1$ to $C_{10}$ hydrocarbyl group; or alternatively a $C_1$ to $C_5$ hydrocarbyl group.

In some embodiments each of $R^1$ and $R^2$ may be independently selected from the group consisting of a halide, an alkyl group, a cycloalkyl group, a substituted cycloalkyl group, an aryl group, a substituted aryl group, a heteroaryl group, and a substituted heteroaryl group. In other embodiments, each of $R^1$ and $R^2$ may independently be a halide, an alkyl group, a cycloalkyl group, a substituted cycloalkyl group, an aryl group, or a substituted aryl group; alternatively, a halide; alternatively an alkyl group; alternatively, a cycloalkyl group or a substituted cycloalkyl group; alternatively, an aryl group or a substituted aryl group; or alternatively, a heteroaryl group or a substitute heteroaryl group. In yet other embodiments, each of $R^1$ and $R^2$ may independently be a halide, alternatively, an alkyl group; alternatively, a cycloalkyl group; alternatively, a substituted cycloalkyl group; alternatively, an aryl group; alternatively, a substituted aryl group; alternatively, a heteroaryl group; or alternatively, a substituted heteroaryl group.

In an embodiment, each of $R^1$ and $R^2$ may independently be a fluoride, chloride, bromide, or iodide; alternatively, a fluoride or chloride; alternatively, a chloride. In some embodiments, at least two of $R^1$ and $R^2$ are a halide; alternatively, $R^1$ and/or $R^2$ are chloride.

In an embodiment, the alkyl group which may be utilized as a $R^1$ and/or $R^2$ group may be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, the alkyl group which may be utilized as a $R^1$ and/or $R^2$ group may be a methyl group, an ethyl group, a n-propyl group, an iso-propyl group, a n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

In an embodiment, the cycloalkyl group which may be utilized as a $R^1$ and/or $R^2$ group may be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, the cycloalkyl group which may be utilized as a $R^1$ and/or $R^2$ group may be a cyclopentyl group, a substituted cyclopentyl group, a cyclohexyl group, or a substituted cyclohexyl group. In other embodiments, the cycloalkyl group which may be utilized as a $R^1$ and/or $R^2$ group may be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group, or a substituted cyclooctyl group. In further embodiments, the cycloalkyl group which may be utilized as a $R^1$ and/or $R^2$ group may be a cyclopentyl group; alternatively, a substituted cyclopentyl group; a cyclohexyl group; or alternatively, a substituted cyclohexyl group. Substituents for the substituted cycloalkyl group are independently disclosed herein and may be utilized without limitation to further describe the substituted cycloalkyl group which may be utilized as a $R^1$ and/or $R^2$ group.

In an aspect, the aryl group(s) which may be utilized as a $R^1$ and/or $R^2$ group may be a phenyl group, a substituted phenyl group, a naphthyl group, or a substituted naphthyl group. In an embodiment, the aryl group(s) which may be utilized as a $R^1$ and/or $R^2$ group may be a phenyl group or a substituted phenyl group; alternatively, a naphthyl group or a substituted naphthyl group; alternatively, a phenyl group or a naphthyl group; or alternatively, a substituted phenyl group or a substituted naphthyl group.

In an embodiment, the substituted phenyl group which may be utilized as a $R^1$ and/or $R^2$ group may be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, the substituted phenyl group which may be utilized as a $R^1$ and/or $R^2$ group may be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group.

In an embodiment, each non-hydrogen substituent(s) for the substituted cycloalkyl group, substituted aryl group, or substituted heteroaryl group which may be utilized as a $R^1$ and/or $R^2$ group may be independently selected from a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In some embodiments, each non-hydrogen substituent(s) for the substituted cycloalkyl group, substituted aryl group, or substituted heteroaryl group which may be utilized as a $R^1$ and/or $R^2$ group may be independently selected from a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group. Specific substituent halides, hydrocarbyl groups, and hydrocarboxy groups are independently disclosed herein and may be utilized without limitation to further describe the substituents for the substituted cycloalkyl group, substituted aryl group, or substituted heteroaryl group which may be utilized as a $R^1$ and/or $R^2$ group.

In an embodiment, any halide substituent of a substituted cycloalkyl group (general or specific), substituted aryl group (general or specific), substituted heteroaryl (general or specific) may be a fluoride, chloride, bromide, or iodide; alternatively, a fluoride or chloride. In some embodiments, any halide substituent of a substituted cycloalkyl group (general or specific), substituted aryl group (general or specific), substituted heteroaryl (general or specific) may be a fluoride; alternatively, a chloride; alternatively, a bromide; or alternatively, an iodide.

In an embodiment, any hydrocarbyl substituent of a substituted cycloalkyl group (general or specific), substituted aryl group (general or specific), or substituted heteroaryl (general or specific) may be an alkyl group, an aryl group, or an aralkyl group; alternatively, an alkyl group; alternatively, an aryl group, or an aralkyl group. Generally, the alkyl, aryl, and aralkyl substituent groups may have the same number of carbon atoms as the hydrocarbyl substituent group disclosed herein. In an embodiment, any alkyl substituent of a substituted cycloalkyl group (general or specific), substituted aryl group (general or specific), substituted heteroaryl (general or specific) may be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of a substituted cycloalkyl group (general or specific), substituted aryl group (general or specific), substituted heteroaryl (general or specific) may be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of a substituted cycloalkyl group (general or specific), substituted aryl group (general or specific), substituted heteroaryl (general or specific) may be benzyl group.

In an embodiment, any hydrocarboxy substituent of a substituted cycloalkyl group (general or specific), substituted aryl group (general or specific), substituted heteroaryl (general or specific) may be an alkoxy group, an aryloxy group, or and aralkoxy group; alternatively, an alkoxy group; alternatively, an aryloxy group, or an aralkoxy group. Generally, the alkoxy, aryloxy, and aralkoxy substituent groups may have the same number of carbon atoms as the hydrocarboxy substituent group disclosed herein. In an embodiment, any alkoxy substituent of a substituted cycloalkyl group (general or specific), substituted aryl group (general or specific), substituted heteroaryl (general or specific) may be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aroxy substituent of a substituted cycloalkyl group (general or specific), substituted aryl group (general or specific), substituted heteroaryl (general or specific) may be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of a substituted cycloalkyl group (general or specific), substituted aryl group (general or specific), substituted heteroaryl (general or specific) may be benzoxy group.

In an embodiment, a transition metal complex suitable for use in this disclosure comprises $Cp^*Cr(CH_3)_2(py)$ as represented by Formula I.

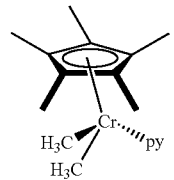

Formula I

In an embodiment, a transition metal complex suitable for use in this disclosure comprises $Cp'Cr(Cl)_2(THF)$ as represented by Formula II.

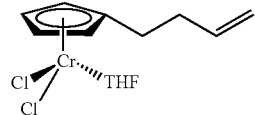

Formula II

In an embodiment, a transition metal complex suitable for use in this disclosure comprises $Cp''Cr(Cl)_2(THF)$ as represented by Formula III.

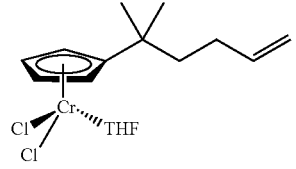

Formula III

Alternatively the catalyst system comprises more than one of the transition metal complexes.

A catalyst system for preparation of a BIP may further comprise an activator-support. The present disclosure encompasses various catalyst compositions containing an activator, which can be an activator-support. In one aspect, the activator-support comprises a chemically-treated solid oxide. Alternatively, the activator-support can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or any combination thereof.

Generally, chemically-treated solid oxides exhibit enhanced acidity as compared to the corresponding untreated solid oxide compound. The chemically-treated solid oxide also functions as a catalyst activator as compared to the corresponding untreated solid oxide. While the chemically-treated solid oxide activates the metallocene(s) in the absence of co-catalysts, it is not necessary to eliminate co-catalysts from the catalyst composition. The activation function of the activator-support is evident in the enhanced activity of catalyst composition as a whole, as compared to a catalyst composition containing the corresponding untreated solid oxide. However, it is believed that the chemically-treated solid oxide can function as an activator, even in the absence of an organoaluminum compound, aluminoxanes, organoboron or organoborate compounds, ionizing ionic compounds, and the like.

The chemically-treated solid oxide can comprise a solid oxide treated with an electron-withdrawing anion. While not intending to be bound by the following statement, it is believed that treatment of the solid oxide with an electron-withdrawing component augments or enhances the acidity of the oxide. Thus, either the activator-support exhibits Lewis or Brønsted acidity that is typically greater than the Lewis or Brønsted acid strength of the untreated solid oxide, or the activator-support has a greater number of acid sites than the untreated solid oxide, or both. One method to quantify the acidity of the chemically-treated and untreated solid oxide materials is by comparing the polymerization activities of the treated and untreated oxides under acid catalyzed reactions.

Chemically-treated solid oxides of this disclosure are formed generally from an inorganic solid oxide that exhibits Lewis acidic or Brønsted acidic behavior and has a relatively high porosity. The solid oxide is chemically-treated with an electron-withdrawing component, typically an electron-withdrawing anion, to form an activator-support.

According to one aspect of the present disclosure, the solid oxide used to prepare the chemically-treated solid oxide has a pore volume greater than about 0.1 cc/g. According to another aspect of the present disclosure, the solid oxide has a pore volume greater than about 0.5 cc/g. According to yet another aspect of the present disclosure, the solid oxide has a pore volume greater than about 1.0 cc/g.

In another aspect, the solid oxide has a surface area of from about 100 to about 1000 m$^2$/g. In yet another aspect, the solid oxide has a surface area of from about 200 to about 800 m$^2$/g. In still another aspect of the present disclosure, the solid oxide has a surface area of from about 250 to about 600 m$^2$/g.

The chemically-treated solid oxide can comprise a solid inorganic oxide comprising oxygen and one or more elements selected from Group 2, 3, 4, 5, 6, 7, 8, 9, 10, 11, 12, 13, 14, or 15 of the periodic table, or comprising oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used to form the chemically-treated solid oxide include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. For example, the solid oxide can comprise silica, alumina, silica-alumina, silica-coated alumina, aluminum phosphate, aluminophosphate, heteropolytungstate, titania, zirconia, magnesia, boria, zinc oxide, mixed oxides thereof, or any combination thereof.

The solid oxide of this disclosure encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Examples of mixed oxides that can be used in the activator-support of the present disclosure include, but are not limited to, silica-alumina, silica-titania, silica-zirconia, zeolites, various clay minerals, alumina-titania, alumina-zirconia, zinc-aluminate, alumina-boria, silica-boria, aluminophosphate-silica, titania-zirconia, and the like. The solid oxide of this disclosure also encompasses oxide materials such as silica-coated alumina, as described in U.S. Patent Publication No. 2010-0076167, the disclosure of which is incorporated herein by reference in its entirety.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect of the present disclosure, the electron-withdrawing component is an electron-withdrawing anion derived from a salt, an acid, or other compound, such as a volatile organic compound, that serves as a source or precursor for that anion. Examples of electron-withdrawing anions include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, and the like, including mixtures and combinations thereof. In addition, other ionic or non-ionic compounds that serve as sources for these electron-withdrawing anions also can be employed in the present disclosure. It is contemplated that the electron-withdrawing anion can be, or can comprise, fluoride, chloride, bromide, phosphate, triflate, bisulfate, or sulfate, and the like, or any combination thereof, in some aspects of this disclosure. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or any combination thereof.

Thus, for example, the activator-support (e.g., chemically-treated solid oxide) used in the catalyst compositions of the present disclosure (e.g., BIP) can be, or can comprise, fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In one aspect, the activator-support can be, or can comprise, fluorided alumina, sulfated alumina, fluorided silica-alumina, sulfated silica-alumina, fluorided silica-coated alumina, sulfated silica-coated alumina, phosphated silica-coated alumina, and the like, or any combination thereof. In another aspect, the activator-support comprises fluorided alumina; alternatively, comprises chlorided alumina; alternatively, comprises sulfated alumina; alternatively, comprises fluorided silica-alumina; alternatively, comprises sulfated silica-alumina; alternatively, comprises fluorided silica-zirconia; alternatively, comprises chlorided silica-zirconia; or alternatively, comprises fluorided silica-coated alumina.

When the electron-withdrawing component comprises a salt of an electron-withdrawing anion, the counterion or cation of that salt can be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, $H^+$, $[H(OEt_2)_2]^+$, and the like.

Further, combinations of one or more different electron-withdrawing anions, in varying proportions, can be used to tailor the specific acidity of the activator-support to the desired level. Combinations of electron-withdrawing components can be contacted with the oxide material simultaneously or individually, and in any order that affords the desired chemically-treated solid oxide acidity. For example, one aspect of this disclosure is employing two or more electron-withdrawing anion source compounds in two or more separate contacting steps.

Thus, one example of such a process by which a chemically-treated solid oxide is prepared is as follows: a selected solid oxide, or combination of solid oxides, is contacted with a first electron-withdrawing anion source compound to form a first mixture; this first mixture is calcined and then contacted with a second electron-withdrawing anion source compound to form a second mixture; the second mixture is then calcined to form a treated solid oxide. In such a process, the first and second electron-withdrawing anion source compounds can be either the same or different compounds.

According to another aspect of the present disclosure, the chemically-treated solid oxide comprises a solid inorganic oxide material, a mixed oxide material, or a combination of inorganic oxide materials, that is chemically-treated with an electron-withdrawing component, and optionally treated with a metal source, including metal salts, metal ions, or other metal-containing compounds. Nonlimiting examples of the metal or metal ion include zinc, nickel, vanadium, titanium, silver, copper, gallium, tin, tungsten, molybdenum, zirconium, and the like, or combinations thereof. Examples of chemically-treated solid oxides that contain a metal or metal ion include, but are not limited to, chlorided zinc-impregnated alumina, fluorided titanium-impregnated alumina, fluorided zinc-impregnated alumina, chlorided zinc-impregnated silica-alumina, fluorided zinc-impregnated silica-alumina, sulfated zinc-impregnated alumina, chlorided zinc aluminate, fluorided zinc aluminate, sulfated zinc aluminate, silica-coated alumina treated with hexafluorotitanic acid, silica-coated alumina treated with zinc and then fluorided, and the like, or any combination thereof.

Any method of impregnating the solid oxide material with a metal can be used. The method by which the oxide is contacted with a metal source, typically a salt or metal-containing compound, can include, but is not limited to, gelling, co-gelling, impregnation of one compound onto another, and the like. If desired, the metal-containing compound is added to or impregnated into the solid oxide in solution form, and subsequently converted into the supported metal upon calcining. Accordingly, the solid inorganic oxide can further comprise a metal selected from zinc, titanium, nickel, vanadium, silver, copper, gallium, tin, tungsten, molybdenum, and the like, or combinations of these metals. For example, zinc is often used to impregnate the solid oxide because it can provide improved catalyst activity at a low cost.

The solid oxide can be treated with metal salts or metal-containing compounds before, after, or at the same time that the solid oxide is treated with the electron-withdrawing anion. Following any contacting method, the contacted mixture of solid compound, electron-withdrawing anion, and the metal ion is typically calcined. Alternatively, a solid oxide material, an electron-withdrawing anion source, and the metal salt or metal-containing compound are contacted and calcined simultaneously.

Various processes are used to form the chemically-treated solid oxide useful in the present disclosure. The chemically-treated solid oxide can comprise the contact product of one or more solid oxides with one or more electron-withdrawing anion sources. It is not required that the solid oxide be calcined prior to contacting the electron-withdrawing anion source. The contact product typically is calcined either during or after the solid oxide is contacted with the electron-withdrawing anion source. The solid oxide can be calcined or uncalcined. Various processes to prepare solid oxide activator-supports that can be employed in this disclosure have been reported. For example, such methods are described in U.S. Pat. Nos. 6,107,230; 6,165,929; 6,294,494; 6,300,271; 6,316,553; 6,355,594; 6,376,415; 6,388,017; 6,391,816; 6,395,666; 6,524,987; 6,548,441; 6,548,442; 6,576,583; 6,613,712; 6,632,894; 6,667,274; 6,750,302; 7,226,886; 7,294,599; 7,601,655; and 7,732,542 the disclosures of which are incorporated herein by reference in their entirety.

According to one aspect of the present disclosure, the solid oxide material is chemically-treated by contacting it with an electron-withdrawing component, typically an electron-withdrawing anion source. Further, the solid oxide material optionally is chemically treated with a metal ion, and then calcined to form a metal-containing or metal-impregnated chemically-treated solid oxide. According to another aspect of the present disclosure, the solid oxide material and electron-withdrawing anion source are contacted and calcined simultaneously.

The method by which the oxide is contacted with the electron-withdrawing component, typically a salt or an acid of an electron-withdrawing anion, can include, but is not limited to, gelling, co-gelling, impregnation of one compound onto another, and the like. Thus, following any contacting method, the contacted mixture of the solid oxide, electron-withdrawing anion, and optional metal ion, is calcined.

The solid oxide activator-support (i.e., chemically-treated solid oxide) thus can be produced by a process comprising:

1) contacting a solid oxide (or solid oxides) with an electron-withdrawing anion source compound (or compounds) to form a first mixture; and 2) calcining the first mixture to form the solid oxide activator-support.

According to another aspect of the present disclosure, the solid oxide activator-support (chemically-treated solid oxide) is produced by a process comprising:

1) contacting a solid oxide (or solid oxides) with a first electron-withdrawing anion source compound to form a first mixture;

2) calcining the first mixture to produce a calcined first mixture;

3) contacting the calcined first mixture with a second electron-withdrawing anion source compound to form a second mixture; and 4) calcining the second mixture to form the solid oxide activator-support.

According to yet another aspect of the present disclosure, the chemically-treated solid oxide is produced or formed by contacting the solid oxide with the electron-withdrawing anion source compound, where the solid oxide compound is calcined before, during, or after contacting the electron-withdrawing anion source, and where there is a substantial absence of aluminoxanes, organoboron or organoborate compounds, and ionizing ionic compounds.

Calcining of the treated solid oxide generally is conducted in an ambient atmosphere, typically in a dry ambient atmosphere, at a temperature from about 200° C. to about 900° C., and for a time of about 1 minute to about 100 hours. Calcining can be conducted at a temperature of from about 300° C. to about 800° C., or alternatively, at a temperature of from about 400° C. to about 700° C. Calcining can be conducted for about 30 minutes to about 50 hours, or for about 1 hour to about 15 hours. Thus, for example, calcining can be carried out for about 1 to about 10 hours at a temperature of from about 350° C. to about 550° C. Any suitable ambient atmosphere can be employed during calcining. Generally, calcining is conducted in an oxidizing atmosphere, such as air. Alternatively, an inert atmosphere, such as nitrogen or argon, or a reducing atmosphere, such as hydrogen or carbon monoxide, can be used.

According to one aspect of the present disclosure, the solid oxide material is treated with a source of halide ion, sulfate ion, or a combination of anions, optionally treated with a metal ion, and then calcined to provide the chemically-treated solid oxide in the form of a particulate solid. For example, the solid oxide material can be treated with a source of sulfate (termed a "sulfating agent"), a source of chloride ion (termed a "chloriding agent"), a source of fluoride ion (termed a "fluoriding agent"), or a combination thereof, and calcined to provide the solid oxide activator. Useful acidic activator-supports include, but are not limited to, bromided alumina, chlorided alumina, fluorided alumina, sulfated alumina, bromided silica-alumina, chlorided silica-alumina, fluorided silica-alumina, sulfated silica-alumina, bromided silica-zirconia, chlorided silica-zirconia, fluorided silica-zirconia, sulfated silica-zirconia, fluorided silica-titania, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of these activator-supports optionally can be treated with a metal ion.

The chemically-treated solid oxide can comprise a fluorided solid oxide in the form of a particulate solid. The fluorided solid oxide can be formed by contacting a solid oxide with a fluoriding agent. The fluoride ion can be added to the oxide by forming a slurry of the oxide in a suitable solvent such as alcohol or water including, but not limited to, the one to three carbon alcohols because of their volatility and low surface tension. Examples of suitable fluoriding agents include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4PF_6$), hexafluorotitanic acid ($H_2TiF_6$), ammonium hexafluorotitanic acid (($NH_4)_2TiF_6$), hexafluorozirconic acid ($H_2ZrF_6$), $AlF_3$, $NH_4AlF_4$, analogs thereof, and combinations thereof. Triflic acid and ammonium triflate also can be employed. For example, ammonium bifluoride ($NH_4HF_2$) can be used as the fluoriding agent, due to its ease of use and availability.

If desired, the solid oxide is treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Examples of volatile organic fluoriding agents useful in this aspect of the disclosure include, but are not limited to, freons, perfluorohexane, perfluorobenzene, fluoromethane, trifluoroethanol, and the like, and combinations thereof. Calcining temperatures generally must be high enough to decompose the compound and release fluoride. Gaseous hydrogen fluoride (HF) or fluorine ($F_2$) itself also can be used with the solid oxide if fluorided while calcining. Silicon tetrafluoride ($SiF_4$) and compounds containing tetrafluoroborate ($BF_4$) also can be employed. One convenient method of contacting the solid oxide with the fluoriding agent is to vaporize a fluoriding agent into a gas stream used to fluidize the solid oxide during calcination.

Similarly, in another aspect of this disclosure, the chemically-treated solid oxide comprises a chlorided solid oxide in the form of a particulate solid. The chlorided solid oxide is formed by contacting a solid oxide with a chloriding agent. The chloride ion can be added to the oxide by forming a slurry of the oxide in a suitable solvent. The solid oxide can be treated with a chloriding agent during the calcining step. Any chloriding agent capable of serving as a source of chloride and thoroughly contacting the oxide during the calcining step can be used, such as $SiCl_4$, $SiMe_2Cl_2$, $TiCl_4$, $BCl_3$, and the like, including mixtures thereof. Volatile organic chloriding agents can be used. Examples of suitable volatile organic chloriding agents include, but are not limited to, certain freons, perchlorobenzene, chloromethane, dichloromethane, chloroform, carbon tetrachloride, trichloroethanol, and the like, or any combination thereof. Gaseous hydrogen chloride or chlorine itself also can be used with the solid oxide during calcining. One convenient method of contacting the oxide with the chloriding agent is to vaporize a chloriding agent into a gas stream used to fluidize the solid oxide during calcination.

The amount of fluoride or chloride ion present before calcining the solid oxide generally is from about 1 to about 50% by weight, where the weight percent is based on the weight of the solid oxide, for example, silica-alumina, before calcining. According to another aspect of this disclosure, the amount of fluoride or chloride ion present before calcining the solid oxide is from about 1 to about 25% by weight, and according to another aspect of this disclosure, from about 2 to about 20% by weight. According to yet another aspect of this disclosure, the amount of fluoride or chloride ion present before calcining the solid oxide is from about 4 to about 10% by weight. Once impregnated with halide, the halided oxide can be dried by any suitable method including, but not limited to, suction filtration followed by evaporation, drying under vacuum, spray drying, and the like, although it is also possible to initiate the calcining step immediately without drying the impregnated solid oxide.

The silica-alumina used to prepare the treated silica-alumina typically has a pore volume greater than about 0.5 cc/g. According to one aspect of the present disclosure, the pore volume is greater than about 0.8 cc/g, and according to another aspect of the present disclosure, greater than about 1.0 cc/g. Further, the silica-alumina generally has a surface area greater than about 100 m$^2$/g. According to another aspect of this disclosure, the surface area is greater than about 250 m$^2$/g. Yet, in another aspect, the surface area is greater than about 350 m$^2$/g.

The silica-alumina utilized in the present disclosure typically has an alumina content from about 5 to about 95% by weight. According to one aspect of this disclosure, the alumina content of the silica-alumina is from about 5 to about 50%, or from about 8% to about 30%, alumina by weight. In another aspect, high alumina content silica-alumina compounds can employed, in which the alumina content of these silica-alumina compounds typically ranges from about 60% to about 90%, or from about 65% to about 80%, alumina by weight. According to yet another aspect of this disclosure, the solid oxide component comprises alumina without silica, and according to another aspect of this disclosure, the solid oxide component comprises silica without alumina.

The sulfated solid oxide comprises sulfate and a solid oxide component, such as alumina or silica-alumina, in the form of a particulate solid. Optionally, the sulfated oxide is treated further with a metal ion such that the calcined sulfated oxide comprises a metal. According to one aspect of the present disclosure, the sulfated solid oxide comprises sulfate and alumina. In some instances, the sulfated alumina is formed by a process wherein the alumina is treated with a sulfate source, for example, sulfuric acid or a sulfate salt such as ammonium sulfate. This process is generally performed by forming a slurry of the alumina in a suitable solvent, such as alcohol or water, in which the desired concentration of the sulfating agent has been added. Suitable organic solvents include, but are not limited to, the one to three carbon alcohols because of their volatility and low surface tension.

According to one aspect of this disclosure, the amount of sulfate ion present before calcining is from about 0.5 to about 100 parts by weight sulfate ion to about 100 parts by weight solid oxide. According to another aspect of this disclosure, the amount of sulfate ion present before calcining is from about 1 to about 50 parts by weight sulfate ion to about 100 parts by weight solid oxide, and according to still another aspect of this disclosure, from about 5 to about 30 parts by weight sulfate ion to about 100 parts by weight solid oxide. These weight ratios are based on the weight of the solid oxide before calcining. Once impregnated with sulfate, the sulfated oxide can be dried by any suitable method including, but not limited to, suction filtration followed by evaporation, drying under vacuum, spray drying, and the like, although it is also possible to initiate the calcining step immediately.

According to another aspect of the present disclosure, the activator-support used in preparing the catalyst compositions of this disclosure comprises an ion-exchangeable activator-support, including but not limited to silicate and aluminosilicate compounds or minerals, either with layered or non-layered structures, and combinations thereof. In another aspect of this disclosure, ion-exchangeable, layered aluminosilicates such as pillared clays are used as activator-supports. When the acidic activator-support comprises an ion-exchangeable activator-support, it can optionally be treated with at least one electron-withdrawing anion such as those disclosed herein, though typically the ion-exchangeable activator-support is not treated with an electron-withdrawing anion.

According to another aspect of the present disclosure, the activator-support of this disclosure comprises clay minerals having exchangeable cations and layers capable of expanding. Typical clay mineral activator-supports include, but are not limited to, ion-exchangeable, layered aluminosilicates such as pillared clays. Although the term "support" is used, it is not meant to be construed as an inert component of the catalyst composition, but rather is to be considered an active part of the catalyst composition, because of its intimate association with the metallocene component.

According to another aspect of the present disclosure, the clay materials of this disclosure encompass materials either in their natural state or that have been treated with various ions by wetting, ion exchange, or pillaring. Typically, the clay material activator-support of this disclosure comprises clays that have been ion exchanged with large cations, including polynuclear, highly charged metal complex cations. However, the clay material activator-supports of this disclosure also encompass clays that have been ion exchanged with simple salts, including, but not limited to, salts of Al(III), Fe(II), Fe(III), and Zn(II) with ligands such as halide, acetate, sulfate, nitrate, or nitrite.

According to another aspect of the present disclosure, the activator-support comprises a pillared clay. The term "pillared clay" is used to refer to clay materials that have been ion exchanged with large, typically polynuclear, highly charged metal complex cations. Examples of such ions include, but are not limited to, Keggin ions which can have charges such as 7+, various polyoxometallates, and other large ions. Thus, the term pillaring refers to a simple exchange reaction in which the exchangeable cations of a clay material are replaced with large, highly charged ions, such as Keggin ions. These polymeric cations are then immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure is maintained and the porosity is enhanced. The resulting pores can vary in shape and size as a function of the pillaring material and the parent clay material used. Examples of pillaring and pillared clays are found in: T. J. Pinnavaia, *Science* 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. Nos. 4,452,910; 5,376,611; and 4,060,480; the disclosures of which are incorporated herein by reference in their entirety.

The pillaring process utilizes clay minerals having exchangeable cations and layers capable of expanding. Any pillared clay that can enhance the polymerization of olefins in the catalyst composition of the present disclosure can be used. Therefore, suitable clay minerals for pillaring include, but are not limited to, allophanes; smectites, both dioctahedral (Al) and tri-octahedral (Mg) and derivatives thereof such as montmorillonites (bentonites), nontronites, hectorites, or LAPONITE® (manufactured by Rockwood Additives Limited); halloysites; vermiculites; micas; fluoromicas; chlorites; mixed-layer clays; the fibrous clays including but not limited to sepiolites, attapulgites, and palygorskites; a serpentine clay; illite; LAPONITE® (manufactured by Rockwood Additives Limited); saponite; and any combination thereof. In one aspect, the pillared clay activator-support comprises bentonite or montmorillonite. The principal component of bentonite is montmorillonite.

The pillared clay can be pretreated if desired. For example, a pillared bentonite is pretreated by drying at about 300° C. under an inert atmosphere, typically dry nitrogen, for about 3 hours, before being added to the polymerization reactor. Although an exemplary pretreatment is described herein, it should be understood that the preheating can be carried out at many other temperatures and times, including any combination of temperature and time steps, all of which are encompassed by this disclosure.

The activator-support used to prepare the catalyst compositions of the present disclosure can be combined with other inorganic support materials, including, but not limited to, zeolites, inorganic oxides, phosphated inorganic oxides, and the like. In one aspect, typical support materials that are used include, but are not limited to, silica, silica-alumina, alumina, titania, zirconia, magnesia, boria, thoria, aluminophosphate, aluminum phosphate, silica-titania, coprecipitated silica/titania, mixtures thereof, or any combination thereof.

According to another aspect of the present disclosure, one or more of the metallocene compounds can be precontacted with an olefin monomer and an organoaluminum compound for a first period of time prior to contacting this mixture with the activator-support. Once the precontacted mixture of the metallocene compound(s), olefin monomer, and organoaluminum compound is contacted with the activator-support, the composition further comprising the activator-support is termed a "postcontacted" mixture. The postcontacted mixture can be allowed to remain in further contact for a second period of time prior to being charged into the reactor in which the polymerization process will be carried out.

According to yet another aspect of the present disclosure, one or more of the metallocene compounds can be precontacted with an olefin monomer and an activator-support for a first period of time prior to contacting this mixture with the organoaluminum compound. Once the precontacted mixture of the metallocene compound(s), olefin monomer, and activator-support is contacted with the organoaluminum compound, the composition further comprising the organoaluminum is termed a "postcontacted" mixture. The postcontacted mixture can be allowed to remain in further contact for a second period of time prior to being introduced into the polymerization reactor.

In an embodiment, the activator or activator-support is present in the catalyst system (i.e., BIP) in an amount of from about 1 wt. % to about 90 wt. %, alternatively from about 5 wt. % to about 90 wt. %, alternatively from about 10 wt. % to about 90 wt. % based on the total weight of catalyst. In an embodiment, the weight ratio of metallocene compound(s) to activator-support is in a range from about 1:1 to about 1:1,000,000. If more than one activator-support is employed, this ratio is based on the total weight of the activator-support. In another embodiment, this weight ratio is in a range from about 1:5 to about 1:100,000, or from about 1:10 to about 1:10,000. Yet, in another aspect, the weight ratio of the metallocene compound(s) to the activator-support is in a range from about 1:20 to about 1:1000.

In an embodiment, a catalyst system of the type disclosed herein comprises an activator-support (or activator) which comprises a chemically-treated solid oxide (e.g., sulfated alumina). The catalyst system comprising a chemically-treated solid oxide may function as described herein in the absence of any additional activators. In an embodiment, a catalyst system of the type described herein comprises a chemically-treated solid oxide as an activator and excludes additional activators. In an alternative embodiment, a catalyst system of the type described herein comprises a chemically treated solid oxide as an activator and at least one additional activator.

In an embodiment, the additional activator comprises an aluminoxane compound. As used herein, the term "aluminoxane" refers to aluminoxane compounds, compositions, mixtures, or discrete species, regardless of how such aluminoxanes are prepared, formed or otherwise provided. Aluminoxanes are also referred to as poly(hydrocarbyl aluminum oxides) or organoaluminoxanes.

The aluminoxane compound of this disclosure can be an oligomeric aluminum compound comprising linear structures, cyclic structures, or cage structures, or mixtures of all three. Cyclic aluminoxane compounds having the formula:

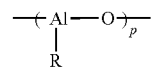

wherein R is a linear or branched alkyl having from 1 to 10 carbon atoms, and p is an integer from 3 to 20, are encompassed by this disclosure. The AlRO moiety shown here also constitutes the repeating unit in a linear aluminoxane. Thus, linear aluminoxanes having the formula:

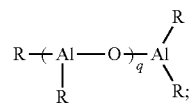

wherein R is a linear or branched alkyl having from 1 to 10 carbon atoms, and q is an integer from 1 to 50, are also encompassed by this disclosure. Further, aluminoxanes suitable for use in this disclosure can have cage structures of the formula $R^t_{5r+\alpha}R^b_{r-\alpha}Al_{4r}O_{3r}$, wherein $R^t$ is a terminal linear or branched alkyl group having from 1 to 10 carbon atoms; $R^b$ is a bridging linear or branched alkyl group having from 1 to 10 carbon atoms; r is 3 or 4; and α is equal to $n_{Al(3)} - n_{O(2)} + n_{O(4)}$, wherein $n_{Al(3)}$ is the number of three coordinate aluminum atoms, $n_{O(2)}$ is the number of two coordinate oxygen atoms, and $n_{O(4)}$ is the number of 4 coordinate oxygen atoms.

In an embodiment, aluminoxanes which can be employed as additional activators in the catalyst compositions of the present disclosure are represented generally by formulas such as $(R-Al-O)_p$, $R(R-Al-O)_qAlR_2$, and the like. In these formulas, the R group is typically a linear or branched $C_1$-$C_6$ alkyl, such as methyl, ethyl, propyl, butyl, pentyl, or hexyl. Examples of aluminoxane compounds that can be used in accordance with the present disclosure include, but are not limited to, methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, or any combination thereof. Methylaluminoxane, ethylaluminoxane, and iso-butylaluminoxane are prepared from trimethylaluminum, triethylaluminum, or triisobutylaluminum, respectively, and sometimes are referred to as poly(methyl aluminum oxide), poly(ethyl aluminum oxide), and poly(isobutyl aluminum oxide), respectively. It is also within the scope of the disclosure to use an aluminoxane in combination with a trialkylaluminum, such as that disclosed in U.S. Pat. No. 4,794,096, incorporated herein by reference in its entirety.

The present disclosure contemplates many values of p and q in the aluminoxane formulas $(R-Al-O)_p$ and $R(R-Al-O)_qAlR_2$, respectively. In some aspects, p and q are at least 3. However, depending upon how the organoaluminoxane is prepared, stored, and used, the value of p and q can vary within a single sample of aluminoxane, and such combinations of organoaluminoxanes are contemplated herein.

In preparing a catalyst composition containing an aluminoxane, the molar ratio of the total moles of aluminum in the aluminoxane (or aluminoxanes) to the total moles of transition metal complex in the composition is generally between about 1:10 and about 100,000:1; alternatively, in a range from about 5:1 to about 15,000:1. Optionally, aluminoxane can be added to a polymerization zone in ranges from about 0.01 mg/L to about 1000 mg/L, from about 0.1 mg/L to about 100 mg/L, or from about 1 mg/L to about 50 mg/L.

In an embodiment, the additional activator comprises comprise an organoboron compound or an organoborate compound. Organoboron or organoborate compounds include neutral boron compounds, borate salts, and the like, or combinations thereof. For example, fluoroorgano boron compounds and fluoroorgano borate compounds are contemplated.

Any fluoroorgano boron or fluoroorgano borate compound can be utilized with the present disclosure. Examples of fluoroorgano borate compounds that can be used in the present disclosure include, but are not limited to, fluorinated aryl borates such as N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and the like, or mixtures thereof. Examples of fluoroorgano boron compounds that can be used in the present disclosure include, but are not limited to, tris(pentafluorophenyl)boron, tris[3,5-bis(trifluoromethyl)phenyl]boron, and the like, or mixtures thereof. Although not intending to be bound by the following theory, these examples of fluoroorgano borate and fluoroorgano boron compounds, and related compounds, are thought to form "weakly-coordinating" anions when combined with organometal compounds, as disclosed in U.S. Pat. No. 5,919,983, the disclosure of which is incorporated herein by reference in its entirety. Applicants also contemplate the use of diboron, or bis-boron, compounds or other bifunctional compounds containing two or more boron atoms in the chemical structure, such as disclosed in J. Am. Chem. Soc., 2005, 127, pp. 14756-14768, the content of which is incorporated herein by reference in its entirety.

Generally, any amount of organoboron compound can be used. According to one aspect of this disclosure, the molar ratio of the total moles of organoboron or organoborate compound (or compounds) to the total moles of metallocene compound (or compounds) in the catalyst composition is in a range from about 0.1:1 to about 15:1. Typically, the amount of the fluoroorgano boron or fluoroorgano borate compound used is from about 0.5 moles to about 10 moles of boron/borate compound per mole of transition metal complex compound. According to another aspect of this disclosure, the amount of fluoroorgano boron or fluoroorgano borate compound is from about 0.8 moles to about 5 moles of boron/borate compound per mole of transition metal complex.

A catalyst system for preparation of a BIP may further comprise a cocatalyst. In an embodiment, the cocatalyst comprises an organoaluminum compound. Such compounds include, but are not limited to, compounds having the formula:

where $R^1$ is an aliphatic group having from 2 to 10 carbon atoms. For example, $R^1$ can be ethyl, propyl, butyl, hexyl, or isobutyl.

Other organoaluminum compounds which can be used in catalyst compositions disclosed herein can include, but are not limited to, compounds having the formula:

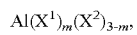

where $X^1$ is a hydrocarbyl; $X^2$ is an alkoxide or an aryloxide, a halide, or a hydride; and m is from 1 to 3, inclusive. In an embodiment, $X^1$ is a hydrocarbyl having from 1 to about 20 carbon atoms; alternatively from 1 to 10 carbon atoms. Non-limiting examples of such hydrocarbyls have been previously disclosed herein. In an embodiment, $X^2$ is an alkoxide or an aryloxide, any one of which has from 1 to 20 carbon atoms, a halide, or a hydride. In an embodiment, $X^2$ is selected independently from fluorine or chlorine, alternatively, $X^2$ is chlorine. In the formula, $Al(X^1)_m(X^2)_{3-m}$, m may be a number from 1 to 3, inclusive, alternatively, m is 3. The value of m is not restricted to be an integer; therefore, this formula includes sesquihalide compounds or other organoaluminum cluster compounds.

Examples of organoaluminum compounds suitable for use in accordance with the present disclosure include, but are not limited to, trialkylaluminum compounds, dialkylaluminum halide compounds, dialkylaluminum alkoxide compounds, dialkylaluminum hydride compounds, and combinations thereof. Specific non-limiting examples of suitable organoaluminum compounds include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof.

Generally, the weight ratio of organoaluminum compound to activator-support is in a range from about 10:1 to about 1:1000. If more than one organoaluminum compound and/or more than one activator-support is employed, this ratio is based on the total weight of each respective component. In another embodiment, the weight ratio of the organoaluminum compound to the activator-support is in a range from about 3:1 to about 1:100, or from about 1:1 to about 1:50.

In an embodiment catalyst system for preparation of a BIP of the type described herein comprises Cp*Cr(CH$_3$)$_2$(py), a sulfated alumina activator support, an optional activator comprising an aluminoxane and an optional cocatalyst comprising an organoaluminum compound. In an embodiment catalyst system for preparation of a BIP of the type described herein comprises Cp'Cr(Cl)$_2$(THF); a sulfated alumina activator support, an optional activator comprising an aluminoxane and an optional cocatalyst comprising an organoaluminum compound. In an embodiment catalyst system for preparation of a BIP of the type described herein comprises Cp"Cr(Cl)$_2$(THF), a sulfated alumina activator support, an optional activator comprising an aluminoxane and an optional cocatalyst comprising an organoaluminum compound.

The catalyst and catalyst systems disclosed herein are intended for any olefin polymerization method which may be carried out using various types of polymerization reactors. As used herein, "polymerization reactor" includes any polymerization reactor capable of polymerizing olefin monomers to produce homopolymers or copolymers. Such homopolymers and copolymers are referred to as resins or polymers.

The various types of reactors include those that may be referred to as batch, slurry, gas-phase, solution, high pressure, tubular or autoclave reactors. Gas phase reactors may comprise fluidized bed reactors or staged horizontal reactors. Slurry reactors may comprise vertical or horizontal loops. High pressure reactors may comprise autoclave or tubular reactors. Reactor types can include batch or continuous processes. Continuous processes could use intermittent or continuous product discharge. Processes may also include partial or full direct recycle of un-reacted monomer, un-reacted co-monomer, and/or diluent.

Polymerization reactor systems of the present disclosure may comprise one type of reactor in a system or multiple reactors of the same or different type. Production of polymers in multiple reactors may include several stages in at least two separate polymerization reactors interconnected by a transfer device making it possible to transfer the polymers resulting from the first polymerization reactor into the second reactor. The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas reactors, a combination of loop and gas reactors, multiple high pressure reactors or a combination of high pressure with loop and/or gas reactors. The multiple reactors may be operated in series or in parallel.

According to one aspect of the disclosure, the polymerization reactor system may comprise at least one loop slurry reactor comprising vertical or horizontal loops. Monomer, diluent, catalyst and optionally any co-monomer may be continuously fed to a loop reactor where polymerization occurs. Generally, continuous processes may comprise the continuous introduction of a monomer, a catalyst, and a diluent into a polymerization reactor and the continuous removal from this reactor of a suspension comprising polymer particles and the diluent. Reactor effluent may be flashed to remove the solid polymer from the liquids that comprise the diluent, monomer and/or co-monomer. Various technologies may be used for this separation step including but not limited to, flashing that may include any combination of heat addition and pressure reduction; separation by cyclonic action in either a cyclone or hydrocyclone; or separation by centrifugation.

A typical slurry polymerization process (also known as the particle form process), is disclosed, for example, in U.S. Pat. Nos. 3,248,179; 4,501,885; 5,565,175; 5,575,979; 6,239,235; 6,262,191; and 6,833,415, each of which is incorporated by reference herein in its entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect of this disclosure, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749; 4,588,790; and 5,436,304, each of which is incorporated by reference herein in its entirety.

According to still another aspect of the disclosure, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another aspect of the disclosure, the polymerization reactor may comprise a solution polymerization reactor wherein the monomer is contacted with the catalyst composition by suitable stirring or other means. A carrier comprising an inert organic diluent or excess monomer may be employed. If desired, the monomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present disclosure may further comprise any combination of at least one raw material feed system, at least one feed system for catalyst or catalyst components, and/or at least one polymer recovery system. Suitable reactor systems for the present disclosure may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide resin properties include temperature, pressure and the concentrations of various reactants. Polymerization temperature can affect catalyst productivity, polymer molecular weight and molecular weight distribution. Suitable polymerization temperature may be any temperature below the de-polymerization temperature according to the Gibbs Free energy equation. Typically this includes from about 60° C. to about 280° C., for example, and from about 70° C. to about 110° C., depending upon the type of polymerization reactor.

Suitable pressures will also vary according to the reactor and polymerization type. The pressure for liquid phase polymerizations in a loop reactor is typically less than 1000 pound-force per square inch gauge (psig). Pressure for gas phase polymerization is usually at about 200 to about 500 psig. High pressure polymerization in tubular or autoclave reactors is generally run at about 20,000 to about 75,000 psig. Polymerization reactors can also be operated in a supercritical region occurring at generally higher temperatures and pressures. Operation above the critical point of a pressure/temperature diagram (supercritical phase) may offer advantages.

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological measurements.

The concentrations of monomer, hydrogen, modifiers, and electron donors are important in producing these resin properties. Hydrogen can be used to control product molecular weight. Modifiers can be used to control product properties and electron donors affect stereoregularity. In addition, the concentration of poisons is minimized because poisons impact the reactions and product properties. In an embodiment, hydrogen is added to the reactor during polymerization. Alternatively, hydrogen is not added to the reactor during polymerization.

The polymer or resin may be formed into various articles, including, but not limited to, bottles, drums, toys, household containers, utensils, film products, drums, fuel tanks, pipes, geomembranes, and liners. Various processes may be used to form these articles, including, but not limited to, blow molding, extrusion molding, rotational molding, injection molding, fiber spinning, thermoforming, cast molding and the like. After polymerization, additives and modifiers can be added to the polymer to provide better processing during manufacturing and for desired properties in the end product. Additives include surface modifiers such as slip agents, antiblocks, tackifiers; antioxidants such as primary and secondary antioxidants; pigments; processing aids such as waxes/oils and fluoroelastomers; and special additives such as fire retardants, antistats, scavengers, absorbers, odor enhancers, and degradation agents.

Catalysts and catalyst systems prepared in accordance with the present disclosure may be used for the polymerization of olefins, for example, alpha-olefins. In an embodiment, a catalyst or catalyst system of the type described herein is contacted with an olefin in a reaction zone under suitable reaction conditions (e.g., temperature, pressure, etc.) to polymerize the olefins. Linear or branched alpha-olefins having 2 to 30 carbon atoms can be used as the olefins raw material. Specific examples of the alpha-olefins may include ethylene, propylene, 1-butene, 1-hexene, 1-octene, 3-methyl-1-butene, 4-methyl-1-pentene, or the like. Such alpha-olefins may be used individually to produce homopolymers. In an embodiment, the catalyst system described herein is used to produce polyethylene, for example, a polyethylene homopolymer or co-polymer.

After polymerization, additives and modifiers can be added to the polymer to provide better processing during manufacturing and for desired properties in the end product. Additives include surface modifiers such as slip agents, antiblocks, tackifiers; antioxidants such as primary and secondary antioxidants; pigments; processing aids such as waxes/oils and fluoroelastomers; and special additives such as fire retardants, antistats, scavengers, absorbers, odor enhancers, and degradation agents.

In an embodiment, a catalyst system of the type described herein when used as a polymerization catalyst may display a catalyst activity in the range of from about 10,000 g(PE)/g (Cr)/h to about 5,000,000 g(PE)/g (Cr)/h; alternatively, from about 20,000 g(PE)/g (Cr)/h to about 4,000,000; alternatively, from about 30,000 g(PE)/g (Cr)/h to about 3,000,000 g(PE)/g (Cr)/h. Catalyst activity is described in terms of grams polyethylene produced per gram of chromium-catalyst per hour (g (PE)/g Cr/h). In an embodiment, the catalyst activity is independent of the reaction temperature in the range of from about 60° C. to about 120° C.; alternatively from about 70° C. to about 115° C.; alternatively from about 80° C. to about 110° C. Herein "independent of the reaction temperature" refers to the catalyst activity varying by less than about 20%, alternatively less than about 15%; alternatively less than about 10% in the disclosed ranges.

In an embodiment, a BIP of the type described herein is a unimodal resin. Herein, the "modality" of a polymer resin refers to the form of its molecular weight distribution curve, i.e., the appearance of the graph of the polymer weight fraction as a function of its molecular weight. The polymer weight fraction refers to the weight fraction of molecules of a given size. A polymer having a molecular weight distribution curve showing a single peak may be referred to as a unimodal polymer, a polymer having curve showing two distinct peaks may be referred to as bimodal polymer, a polymer having a curve showing three distinct peaks may be referred to as trimodal polymer, etc. Two or more peaks may be referred to as multimodal.

In an embodiment, the BIP has a weight average molecular weight ($M_w$) of from about 10,000 g/mol to about 2,500,000 g/mol, alternatively from about 50,000 g/mol to about 2,000,000 g/mol; or alternatively from about 100,000 g/mol to about 1,500,000 g/mol; or alternatively, from about 140,000 g/mol to about 160,000 g/mol and a number average molecular weight ($M_n$) of from about 3,000 g/mol to about 150,000 g/mol, alternatively, from about 4,000 g/mol to about 125,000 g/mol, alternatively, from about 5,000 g/mol to about 100,000 g/mol; or alternatively, from about 8,000 g/mol to about 18,000 g/mol. The weight average molecular weight describes the molecular weight distribution of a polymer composition and is calculated according to equation 1:

$$\overline{M}_w = \frac{\sum_i N_i M_i^2}{\sum_i N_i M_i} \quad (1)$$

where Ni is the number of molecules of molecular weight Mi. All molecular weight averages are expressed in gram per mole (g/mol). The number average molecular weight is the common average of the molecular weights of the individual polymers calculated by measuring the molecular weight of n polymer molecules, summing the weights, and dividing by n.

$$\overline{M}_n = \frac{\sum_i N_i M_i}{\sum_i N_i} \quad (2)$$

The molecular weight distribution (MWD) of the BIP is the ratio of the weight average molecular weight ($M_w$) to the number average molecular weight ($M_n$), which is also referred to as the polydispersity index (PDI) or more simply as polydispersity. The BIP composition may be characterized by a broad molecular weight distribution (MWD). More specifically, the BIP composition may have a PDI from about 2 to about 120, alternatively from about 3 to about 100, alternatively from about 4 to about 80.

The BIP may be characterized by the degree of branching present in the composition. Short chain branching (SCB) is known for its effects on polymer properties such as stiffness, tensile properties, heat resistance, hardness, permeation resistance, shrinkage, creep resistance, transparency, stress crack resistance, flexibility, impact strength, and the solid state properties of semi-crystalline polymers, such as polyethylene, while long chain branching (LCB) exerts its effects on polymer rheology. The BIP composition may contain equal to or less than about one long chain branch (LCB) per about 10,000 total carbon atoms (about 1/10,000), alternatively, equal to or less than about one LCB per about 100,000 total carbon atoms (about 1/100,000), or alternatively, equal to or less than about one LCB per about 1,000,000 total carbon atoms (about 1/1,000,000). In an aspect, LCB in the BIP may be increased using any suitable methodology such as, for example, by treatment with peroxide. In an aspect, the BIP is treated to increase the LCB to from greater than about 0 to about 0.5, alternatively, from greater than about 0 to about 0.25, alternatively, from greater than about 0 to about 0.15, or alternatively, from about 0.01 to about 0.08.

In an embodiment, a BIP of the type described herein is characterized by a density of from about 0.946 g/ml to about 0.97 g/ml, alternatively, from about 0.948 g/ml to about 0.968 g/ml, alternatively, from about 0.95 g/ml to about 0.966 g/ml, or alternatively, from about 0.96 g/ml to about 0.966 g/ml as determined in accordance with ASTM D1505. For example, the BIP may be a high-density polyethylene having a density of greater than about 0.945 g/ml, alternatively, greater than about 0.955 g/ml, alternatively, greater than about 0.958 g/ml.

In an embodiment, a BIP produced using a catalyst of the type described herein has a melt index, MI, in the range of from about 0.01 dg/min. to about 5.0 dg/min., alternatively, from about 0.05 dg/min. to about 4.0 dg/min., alternatively, from about 0.1 dg/min. to about 3.0 dg/min, or alternatively, from about 0.8 dg/min. to about 1.8 dg/min. The melt index (MI) refers to the amount of a polymer which can be forced through an extrusion rheometer orifice of 0.0825 inch diameter when subjected to a force of 2160 grams in ten minutes at 190° C., as determined in accordance with ASTM D 1238.

In an embodiment, a BIP of the type described herein has a Carreau Yasuda 'a' parameter in the range of from about 0.1 to about 0.3, alternatively, from about 0.5 to about 0.6, alternatively, from about 0.51 to about 0.59, alternatively, from about 0.54 to about 0.57. The Carreau Yasuda 'a' parameter (CY-a) is defined as the rheological breadth parameter. Rheological breadth refers to the breadth of the transition region between Newtonian and power-law type shear rate for a polymer or the frequency dependence of the viscosity of the polymer. The rheological breadth is a function of the relaxation time distribution of a polymer resin, which in turn is a function of the resin molecular structure or architecture. The CY-a parameter may be obtained by assuming the Cox-Merz rule and calculated by fitting flow curves generated in linear-viscoelastic dynamic oscillatory frequency sweep experiments with a modified Carreau-Yasuda (CY) model, which is represented by Equation (3):

$$E = E_o[1 + (T_\xi \dot{\gamma})^a]^{\frac{n-1}{a}} \quad (3)$$

where
E=viscosity (Pa·s)
$\dot{\gamma}$=shear rate (1/s)
a=rheological breadth parameter
$T_\xi$=relaxation time (s) [describes the location in time of the transition region]
$E_o$=zero shear viscosity (Pa·s) [defines the Newtonian plateau]
n=power law constant [defines the final slope of the high shear rate region].

To facilitate model fitting, the power law constant n is held at a constant value. Details of the significance and interpretation of the CY model and derived parameters may be found in: C. A. Hieber and H. H. Chiang, *Rheol. Acta*, 28, 321 (1989); C. A. Hieber and H. H. Chiang, *Polym. Eng. Sci.*, 32, 931 (1992); and R. B. Bird, R. C. Armstrong and O. Hasseger, *Dynamics of Polymeric Liquids, Volume 1, Fluid Mechanics*, 2nd Edition, John Wiley & Sons (1987), each of which is incorporated by reference herein in its entirety.

In an embodiment, a BIP of the type described herein has a zero shear viscosity ($E_o$), defined by Equation (3), in the range of from about $3.5 \times 10^3$ Pa-s to about $7 \times 10^4$ Pa-s, alternatively from about $1 \times 10^4$ Pa-s to about $6 \times 10^4$ Pa-s, alternatively from about $1.5 \times 10^4$ Pa-s to about $6 \times 10^4$ Pa-s. The zero shear viscosity refers to the viscosity of the polymeric composition at a zero shear rate and is indicative of the materials molecular structure. Further, for polymer melts, the zero shear viscosity is often a useful indicator of processing attributes such as melt strength in blow-molding and foam technologies and bubble stability in film blowing. For example, the higher the zero shear viscosity, the better the melt strength or bubble stability.

In an embodiment, a BIP of the type described herein has a relaxation time ($\tau$), defined by Equation (3), in the range of from about 0.01 s to about 0.10 s, alternatively, from about 0.01 s to about 0.03 s, alternatively, from about 0.012 s to about 0.08 s, alternatively, from about 0.015 s to about 0.05 s. The relaxation rate refers to the viscous relaxation times of the polymer and is indicative of a distribution of relaxation times associated with the wide distribution of molecular weights.

In an embodiment, a BIP of the type described herein has a shear viscosity at 100 sec$^{-1}$ ($E_{100}$), defined as the viscosity indicative of the head pressure during extrusion, in the range of from about $8 \times 10^2$ Pa-s to about $6 \times 10^4$ Pa-s, alternatively, from about $8 \times 10^2$ Pa-s to about $2 \times 10^3$ Pa-s, alternatively, from about $8 \times 10^2$ Pa-s to about $1.2 \times 10^3$ Pa-s, alternatively, from about $8.5 \times 10^2$ Pa-s to about $1.9 \times 10^3$ Pa-s, alternatively, from about $9 \times 10^2$ Pa-s to about $1.8 \times 10^3$ Pa-s, or alternatively, from about $1 \times 10^4$ Pa-s to about $6 \times 10^4$ Pa-s. This feature is related to the ease of extrusion during the film fabrication and is an indirect comparative measurement of the head pressure generated by the melt extrusion of the polymer in an extruder. In general, a lower head pressure is favorable to higher output rates, i.e., more pounds of material produced per hour of extrusion.

Polymer resins produced as disclosed herein may be formed into articles of manufacture or end use articles using techniques known in the art such as extrusion, blow molding, injection molding, fiber spinning, thermoforming, and casting. For example, a polymer resin may be extruded into a sheet, which is then thermoformed into an end use article such as a container, a cup, a tray, a pallet, a toy, or a component of another product. In an embodiment, the polymer resins produced as described herein (e.g., polyethylene) may be formed into films which can be useful in food packaging.

In an embodiment, the polymer resins of this disclosure are fabricated into a film. The films of this disclosure may be produced by any suitable method and under any suitable condition for the production of films. In an embodiment, the polymer resins are formed into films through a cast film process. In a cast film process, plastic melt is extruded through a slit die onto a chilled, polished roll to freeze the film. The speed of the roll controls the draw down ratio and film gauge. The film moves forward toward a second wounding roll where cooling is completed. The films formed from polymer resins of this disclosure (e.g., polyethylene) may be of any thickness desired by the user. Alternatively, the polymer resins of this disclosure may be formed into films having a thickness of from about 0.3 mil (7 microns) to about 3 mils (76 microns), alternatively, from about 0.5 mil (12 microns)

to about 2 mils (50 microns), alternatively, from about 0.8 mil (20 microns) to about 1.6 mils (40 microns).

Production of films of the type described herein may be facilitated by the use of polymeric resins prepared as described herein. For example, polymeric resins of the type described herein (i.e., BIP) when subjected to the film production process may display improved processing characteristics. In an embodiment, polymer resins of the type described herein may be extruded at a similar extrusion pressure when compared to polymer resin of similar melt index prepared with a dissimilar catalyst system. Such dissimilar catalysts may be conventional catalyst systems such as Ziegler Natta catalysts.

Additional observations in processing may include similar head pressures and motor load are employed in the manufacture process with the resins of this disclosure when compared to resins produced using dissimilar catalyst systems. Herein the head pressure refers to the discharge pressure at the end of the extruder while the motor load refers to horsepower draw of the extruder.

In an embodiment, the BIP comprises a polyethylene homopolymer which is formed into a film that displays enhanced barrier properties. For example said films may display a reduced moisture vapor transmission rate (MVTR).

In an embodiment, a nominally 1.6-1.8 mil thick bound film produced from polymer resins of this disclosure (i.e., BIP) has a gauge-normalized MVTR in the range of from about 0.30 grams·mil per 100 square inch per day (g·mil/100 in$^2$/day) to about 0.85 g·mil/100 in$^2$/day, alternatively, from about 0.3 g·mil/100 in$^2$/day to about 0.6 g·mil/100 in$^2$/day, or alternatively, from about 0.3 g·mil/100 in$^2$/day to about 0.5 g·mil/100 in$^2$/day as measured in accordance with ASTM F 1249. The MVTR measures passage of gaseous H$_2$O through a barrier. The MVTR may also be referred to as the water vapor transmission rate (WVTR). Typically, the MVTR is measured in a special chamber, divided vertically by the substrate/barrier material. A dry atmosphere is in one chamber, and a moist atmosphere is in the other. A 24-hour test is run to see how much moisture passes through the substrate/barrier from the "wet" chamber to the "dry" chamber under conditions which can specify any one of five combinations of temperature and humidity in the "wet" chamber.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner. In the following examples, MVTR was measured in accordance with ASTM F-1249. Following the extrusion of the resin into film, the actual measurement of MVTR is performed using a Mocon Permatran machine (model W 3/31) testing system or equivalent. The Mocon instrument for measuring water permeability was developed by Modern Controls, Inc. To accomplish the MVTR measurement, a 10×10 cm sample is cut from a random area of the film. The sample is then mounted in a sample test cell and placed in the Mocon Permatran W3/31 unit. In the unit, the test film is exposed to a constant continuous flow of dry nitrogen gas across one side of the film (exhaust side) and a constant flow of controlled humidity nitrogen gas across the other side (carrier side). Water vapor passes from the humidified nitrogen side of the test cell through the film and into the dry nitrogen side of the test cell. A modulated infra-red photo-detection system on the exhaust side of the test cell measures the variation in absorption of infra-red energy caused by the water vapor which has transmitted through the film. By comparing the amplitude of the output signal obtained from the infra-red photo-detection system mounted on the test cell with the amplitude of a signal from a reference cell in the same instrument containing a film with a known transmission rate, the transmission rate of the test film is determined. By convention, the value obtained from MVTR is expressed as grams of water transmitted per 100 square inches per one mil (one thousandth of an inch) thickness in a 24-hour period (or, in metric system, grams of water transmitted per square meter per mm thickness in a 24-hour period).

Example 1

Catalyst systems of the type described herein comprising a half-sandwich chromium transition metal complex, a sulfated alumina support and an optional TIBA cocatalyst were prepared. All manipulations were performed under purified nitrogen atmosphere using standard Schlenk line or glovebox techniques. The solvent THF was distilled from potassium, while anhydrous diethyl ether, heptane, pyridine and toluene (Fisher Scientific Company) were stored over activated alumina. All solvents were degassed and stored under nitrogen. Chromium (III) trichloride and all of the organic ligands were purchased from Aldrich Chemical Company. Li($\eta^5$-C$_5$H$_4$CH$_2$CH$_2$CH=CH$_2$) was prepared by the method describe in Brieger, et al., J. Org. Chem. 36 (1971) p 243, and Li($\eta^5$-C$_5$H$_4$C(Me)$_2$CH$_2$CH$_2$CH=CH$_2$) was prepare according to the method used by Bochmann, et al. in J. Organmet. Chem. 592 (1999). Complex (I), Cp*Cr(CH$_3$)$_2$(py), was prepared by the procedure described in Theopold, et al. J. Am. Chem. Soc. 111 (1989) p 9127.

Complex (II) which was Cp'Cr(Cl)$_2$(THF) (Cp'=$\eta^5$-C$_5$H$_4$CH$_2$CH$_2$CH=CH$_2$) was prepared by a procedure involving adding to a THF solution of CrCl$_3$.3THF (1.5 grams, 4.0 mmol) 1 equiv of Li($\eta^5$-C$_5$H$_4$CH$_2$CH$_2$CH=CH$_2$) (0.5 grams, 4.0 mmol) in THF at 0° C. The mixture was stirred at room temperature for 5 hours. After the THF was removed under vacuum, the blue crystal was obtained in a mixture solvent of toluene and heptane at −35° C. (0.3 grams, yield: 31%). Complex (III) which was Cp"Cr(Cl)$_2$(THF) (Cp"=$\eta^5$-C$_5$H$_4$C(Me)$_2$CH$_2$CH$_2$CH=CH$_2$) was prepared by a procedure involving adding to a THF solution of CrCl$_3$.3THF (1.5 grams, 4.0 mmol) 1 equiv of Li($\eta^5$-C$_5$H$_4$C(Me)$_2$CH$_2$CH$_2$CH=CH$_2$) (0.678 grams, 4.0 mmol) in THF at 0° C. The mixture was stirred at room temperature for 5 hours. After the THF was removed under vacuum, the blue crystal was obtained in a mixture solvent of heptanes at −35° C. (0.32 grams, yield: 28%).

The sulfated solid oxide activator support (SSA) was prepared using Alumina A, from W.R. Grace Company, which was impregnated to incipient wetness with an aqueous solution of ammonium sulfate. Typically, the alumina had a surface area of about 330 m$^2$/gram and a pore volume of about 1.3 cc/gram. The amount of ammonium sulfate used was equal to 20% of the starting alumina. The volume of water used to dissolve the ammonium sulfate was calculated from the total pore volume of the starting sample (i.e. 2.6 mL of water for each gram of alumina to be treated). Thus, a solution of about 0.08 grams of ammonium sulfate per mL of water was employed. The resulting wet sand was dried in a vacuum oven overnight at 120° C., and then screened through a 35 mesh screen. Finally, the material was activated in a fluidizing stream of dry air at 550° C. for 6 hours. The samples were then stored under nitrogen.

Catalyst systems comprising Complex (I), (II), or (III), the SSA and a cocatalyst were utilized in the polymerization of ethylene. Generally, all polymerizations were carried out for one hour in a one gallon (3.785 liter) stainless-steel autoclave reactor containing two liters of isobutane as diluent, and hydrogen added from a 325 cc auxiliary vessel. Delta P of hydrogen refers to the pressure drop in that vessel from 600 psig starting pressure. Chromium based half sandwich solutions (1 mg/mL) were usually prepared by dissolving 20 mg of the catalysts precursors in 20 mL of toluene. The reactor was maintained at the desired run temperature through the run by an automated heating-cooling system.

The polymerization procedure could be carried out using one of two general protocols. Using protocol 1, under isobutane purge a TIBA solution (25% in heptanes) was charged to a cold reactor followed by a mixture of half-sandwich chromium complexes and sulfated SSA in toluene. The reactor was closed and 2 Liters isobutane were added. The reactor was quickly heated to within 5 degrees of the run temperature and the ethylene feed was opened, ethylene was fed on demand to maintain the reactor pressure. Hydrogen was then introduced into the reactor during the polymerization process. For copolymerization, 1-hexene was flushed in with the initial ethylene charge. At the end of one hour, the reactor contents were flared; the reactor was purged with nitrogen, and then opened. The polymer powder was dried overnight at 60° C. under vacuum. Using protocol II, under isobutane purge a mixture of TIBA solution (25% in heptanes) and SSA was charged to a cold reactor followed by half-sandwich chromium compounds in toluene. The reactor was closed and 2 Liters isobutane were added. The reactor was quickly heated to within 5 degrees of the run temperature and the ethylene feed was opened, ethylene was fed on demand to maintain the reactor pressure. Hydrogen was then introduced into the reactor during the polymerization process. For copolymerization, 1-hexene was flushed in with the initial ethylene charge. At the end of one hour, the reactor contents were flared; the reactor was purged with nitrogen, and then opened. The polymer powder was dried overnight at 60° C. under vacuum.

For samples prepared using Complex (I) and a sulfated SSA activator support, the polymerization process comprised mixing 0.2 mL of TIBA with 0.15 grams of sulfated SSA in a glass tube under nitrogen. After about one minute, the slurry was added the reactor below 40° C. 0.001 gram of Cp*Cr(CH$_3$)$_2$(py) in 1 mL of toluene was also added to the reactor. The reactor was sealed and 2 L of isobutane were added and stirring started at 700 rpm. As the reactor temperature approached 100° C., H2 (366 psi) and ethylene (555 psi) addition was begun and set point of 105° C. was than rapidly attained. The reactor was held at 105° C. for 60 minutes and then the volatiles were vent to the flare system. This procedure left the polyethylene solid in the reactor. It yielded 221.4 grams of polyethylene (activity, 1,262,069 g(PE)/g (Cr)/h).

For samples prepared using Complex (II) and a sulfated SSA activator support, the polymerization process comprised adding 0.2 mL of TIBA, 0.3 grams of sulfated SSA, and 0.002 grams of Cp'Cr(Cl)$_2$(THF) (Cp'=$\eta^5$-C$_5$H$_4$CH$_2$CH$_2$CH=CH$_2$) in 1 mL of toluene to the reactor respectively under 40° C. The reactor was sealed and 2 L of isobutane were added and stirring started at 700 rpm. As the reactor temperature approached 75° C., ethylene (550 psi) addition was begun and set point of 80° C. was than rapidly attained. The reactor was held at 80° C. for 60 minutes and then the volatiles were vent to the flare system. This procedure left the polyethylene solid in the reactor. It yielded 358.6 grams of polyethylene (activity, 1,083,455 g(PE)/g (Cr)/h).

For samples prepared using Complex (III) and a sulfated SSA activator support, the polymerization process comprised adding 0.2 mL of TIBA, 0.3 grams of sulfated SSA, and 0.002 grams of Cp"Cr(Cl)$_2$(THF) (Cp"=$\eta^5$-C$_5$H$_4$C(Me)$_2$CH$_2$CH$_2$CH=CH$_2$) in 1 mL of toluene to the reactor respectively under 40° C. The reactor was sealed and 2 L of isobutane were added and stirring started at 700 rpm. As the reactor temperature approached 85° C., ethylene (402 psi) addition was begun and set point of 90° C. was than rapidly attained. The reactor was held at 90° C. for 60 minutes and then the volatiles were vent to the flare system. This procedure left the polyethylene solid in the reactor. It yielded 108.1 grams of polyethylene (activity, 366,163 g(PE)/g (Cr)/h).

A total of 48 samples were prepared and the conditions, components and component amounts used in each sample, along with the catalyst activity are summarized in Table 1.

TABLE 1

| Sample No. | Catalysts (gram) | TIBA (mL) | SSA (gram) | Comonomer C6(grams) | Delta P H$_2$ (psi) | Ethylene (psi) | Temp (° C.) | Time (min) | Activity kgPE/mol/h | Activity gPE/gCr/h |
|---|---|---|---|---|---|---|---|---|---|---|
| 1 | I(0.002) | 0.2 | 0.3 | 0 | 0 | 402 | 90 | 54 | 80027 | 1539099 |
| 2 | I(0.002) | 0.2 | 0.3 | 0 | 330 | 461 | 90 | 58 | 72454 | 1393453 |
| 3 | I(0.001) | 0.2 | 0.15 | 0 | 461 | 486 | 90 | 60 | 43808 | 842519 |
| 4 | I(0.001) | 0.2 | 0.15 | 0 | 0 | 490 | 105 | 60 | 70039 | 1347005 |
| 5 | I(0.001) | 0.2 | 0.15 | 0 | 463 | 490 | 105 | 60 | 55723 | 1071675 |
| 6 | I(0.001) | 0.2 | 0.15 | 0 | 263 | 536 | 105 | 60 | 40666 | 782095 |
| 7 | I(0.001) | 0.2 | 0.15 | 0 | 366 | 555 | 105 | 60 | 44578 | 857340 |
| 8 | I(0.001) | 0.2 | 0.15 | 0 | 366 | 555 | 105 | 60 | 65623 | 1262069 |
| 9 | I(0.001) | 0.2 | 0.15 | 0 | 469 | 574 | 105 | 60 | 60050 | 1154901 |
| 10 | I(0.001) | 0.2 | 0.15 | 0 | 520 | 584 | 105 | 60 | 50417 | 969638 |
| 11 | I(0.001) | 0.2 | 0.15 | 18 | 462 | 484 | 90 | 60 | 33226 | 639015 |
| 12 | I(0.001) | 0.2 | 0.15 | 38 | 463 | 484 | 90 | 60 | 33315 | 640725 |
| 13 | I(0.001) | 0.2 | 0.15 | 57 | 463 | 482 | 90 | 60 | 34175 | 657256 |
| 14 | II(0.002) | 0 | 0.3 | 0 | 0 | 402 | 90 | 30 | 0 | 0 |
| 15 | II(0.002) | 0.1 | 0.3 | 0 | 0 | 402 | 90 | 60 | 14861 | 285820 |
| 16 | II(0.002) | 0.2 | 0.3 | 0 | 0 | 402 | 90 | 60 | 31200 | 600040 |
| 17 | II(0.002) | 0.3 | 0.3 | 0 | 0 | 402 | 90 | 60 | 22999 | 442325 |
| 18 | II(0.002) | 0.5 | 0.3 | 0 | 0 | 402 | 90 | 60 | 4619 | 88828 |
| 19 | II(0.002) | 1 | 0.3 | 0 | 0 | 402 | 90 | 60 | 24036 | 462266 |
| 20 | II(0.002) | 2 | 0.3 | 0 | 0 | 402 | 90 | 60 | 21475 | 413018 |
| 21 | II(0.001) | 0.15 | 0 | 0 | 0 | 402 | 90 | 60 | 0 | 0 |
| 22 | II(0.002) | 0.5 | 0.1 | 0 | 0 | 402 | 90 | 60 | 13715 | 263764 |
| 23 | II(0.002) | 0.5 | 0.2 | 0 | 0 | 402 | 90 | 60 | 15521 | 298509 |
| 24 | II(0.002) | 0.5 | 0.3 | 0 | 0 | 402 | 90 | 60 | 24554 | 472237 |

TABLE 1-continued

| Sample No. | Catalysts (gram) | TIBA (mL) | SSA (gram) | Comonomer C6(grams) | Delta P H$_2$ (psi) | Ethylene (psi) | Temp (° C.) | Time (min) | Activity kgPE/mol/h | Activity gPE/gCr/h |
|---|---|---|---|---|---|---|---|---|---|---|
| 25 | II(0.002) | 0.5 | 0.4 | 0 | 0 | 402 | 90 | 60 | 24193 | 465288 |
| 26 | II(0.002) | 0.5 | 0.2(M) | 0 | 0 | 402 | 90 | 30 | 1650 | 31724 |
| 27 | II(0.002) | 0.5 | 0.3 | 0 | 0 | 298 | 70 | 60 | 23643 | 454713 |
| 28 | II(0.002) | 0.5 | 0.3 | 0 | 0 | 348 | 80 | 60 | 25136 | 483416 |
| 29 | II(0.002) | 0.5 | 0.3 | 0 | 0 | 460 | 100 | 60 | 25686 | 493990 |
| 30 | II(0.002) | 0.2 | 0.3 | 0 | 0 | 550 | 80 | 60 | 56335 | 1083455 |
| 31 | II(0.002) | 0.2 | 0.3 | 0 | 18 | 406 | 90 | 60 | 26235 | 504565 |
| 32 | II(0.002) | 0.2 | 0.3 | 0 | 32 | 407 | 90 | 60 | 24774 | 476467 |
| 33 | II(0.002) | 0.2 | 0.3 | 0 | 59 | 409 | 90 | 70 | 27115 | 521485 |
| 34 | II(0.002) | 0.2 | 0.3 | 0 | 100 | 419 | 90 | 60 | 24617 | 473445 |
| 35 | II(0.002) | 0.2 | 0.3 | 0 | 200 | 437 | 90 | 60 | 22811 | 438700 |
| 36 | II(0.002) | 0.2 | 0.3 | 0 | 330 | 461 | 90 | 60 | 19889 | 382503 |
| 37 | II(0.002) | 0.2 | 0.3 | 10 | 200 | 437 | 90 | 60 | 21978 | 422687 |
| 38 | II(0.002) | 0.2 | 0.3 | 20 | 200 | 437 | 90 | 60 | 17721 | 340808 |
| 39 | II(0.002) | 0.2 | 0.3 | 30 | 200 | 437 | 90 | 60 | 18349 | 352893 |
| 40 | II(0.002) | 0.2 | 0.3 | 50 | 200 | 437 | 90 | 60 | 15726 | 302437 |
| 41 | II(0.002) | 0.2 | 0.3 | 100 | 200 | 437 | 90 | 60 | 13935 | 267994 |
| 42 | II(0.002) | 0.2 | 0.3 | 0 | 0 | 490 | 105 | 60 | 19135 | 368000 |
| 43 | II(0.002) | 0.2 | 0.3 | 0 | 263 | 536 | 105 | 60 | 12961 | 249261 |
| 44 | II(0.002) | 0.2 | 0.3 | 0 | 366 | 555 | 105 | 60 | 16165 | 310897 |
| 45 | II(0.002) | 0.2 | 0.3 | 0 | 366 | 555 | 105 | 60 | 18993 | 365281 |
| 46 | II(0.002) | 0.2 | 0.3 | 0 | 469 | 574 | 105 | 60 | 13369 | 257117 |
| 47 | II(0.002) | 0.2 | 0.3 | 0 | 469 | 574 | 105 | 60 | 17092 | 328723 |
| 48 | III(0.002) | 0.2 | 0.3 | 0 | 0 | 402 | 90 | 60 | 19039 | 366163 |

The polymer samples were then subjected to additional characterization. Melt index (MI, g/10 min) was determined in accordance with ASTM D1238 condition F at 190° C. with a 2,160 gram weight. High load melt index (HLMI, g/10 min) was determined in accordance with ASTM D1238 condition E at 190° C. with a 21,600 gram weight. Polymer density was determined in grams per cubic centimeter (g/cc) on a compression molded sample, cooled at about 15° C. per hour, and conditioned for about 40 hours at room temperature in accordance with ASTM D1505 and ASTM D1928, procedure C. Molecular weights and molecular weight distributions were obtained using a PL 220 SEC high temperature chromatography unit (Polymer Laboratories) with trichlorobenzene (TCB) as the solvent, with a flow rate of 1 mL/minute at a temperature of 145° C. BHT (2,6-di-tert-butyl-4-methylphenol) at a concentration of 0.5 g/L was used as a stabilizer in the TCB. An injection volume of 200 μL was used with a nominal polymer concentration of 1.5 mg/mL. Dissolution of the sample in stabilized TCB was carried out by heating at 150° C. for 5 hours with occasional, gentle agitation. The columns used were three PLgel Mixed A LS columns (7.8×300 mm) and were calibrated with a broad linear polyethylene standard (Chevron Phillips Marlex® BHB 5003) for which the molecular weight had been determined. The results of these characterizations are summarized in Table 2.

TABLE 2

| Sample No. | Catalysts (gram) | MI dg/min | HLMI | M$_n$/1000 (kg/mol) | M$_w$/1000 (kg/mol) | M$_z$/1000 (kg/mol) | M$_w$/M$_n$ | Density (gram/cc) |
|---|---|---|---|---|---|---|---|---|
| 1 | I | <0.01 | <0.01 | | | | | |
| 2 | I | <0.01 | <0.01 | | | | | |
| 3 | I | 0.11 | | 24.14 | 220.4 | 935.4 | 9.13 | 0.9605 |
| 5 | I | <0.01 | 0.66 | 69.47 | 1382 | 3075 | 19.89 | |
| 6 | I | 0.06 | 5.38 | 25.29 | 245.3 | 1212 | 9.7 | 0.9586 |
| 7 | I | 0.28 | 19.3 | 19.81 | 190.1 | 1094 | 9.6 | 0.9619 |
| 8 | I | 0.10 | 9.363 | 21.19 | 271.9 | 2103 | 12.83 | 0.9608 |
| 9 | I | 0.40 | 21.16 | 18.39 | 170.9 | 1209 | 9.29 | 0.9628 |
| 10 | I | 0.95 | 41.52 | 9.39 | 180.5 | 1898 | 19.22 | 0.9648 |
| 11 | I | 0.20 | | 18.96 | 217.6 | 1256 | 11.48 | 0.9604 |
| 12 | I | 0.24 | | 12.28 | 201.5 | 1386 | 16.41 | 0.9592 |
| 13 | I | 0.17 | 63.8 | 20.78 | 214.9 | 1102 | 10.34 | 0.9578 |
| 20 | II | <0.01 | <0.01 | 40.19 | 1146 | 3175 | 28.51 | |
| 36 | II | <0.01 | 0.03 | 20.81 | 680.1 | 2305 | 32.68 | |
| 41 | II | <0.01 | <0.01 | 11.42 | 616.3 | 2408 | 53.96 | |
| 43 | II | 0.21 | 15.00 | | | | | |
| 44 | II | 0.43 | 24.95 | 9.59 | 217.8 | 2082 | 22.71 | 0.9610 |
| 45 | II | 0.47 | 27.17 | 14.36 | 225.9 | 2396 | 15.73 | 0.9606 |
| 46 | II | 0.82 | 44.91 | 11.76 | 207.2 | 2350 | 17.62 | 0.9633 |
| 47 | II | 0.84 | 50.03 | 10.23 | 186.8 | 2111 | 18.25 | 0.9628 |
| 48 | III | <0.01 | <0.01 | | | | | |

Figure 2:
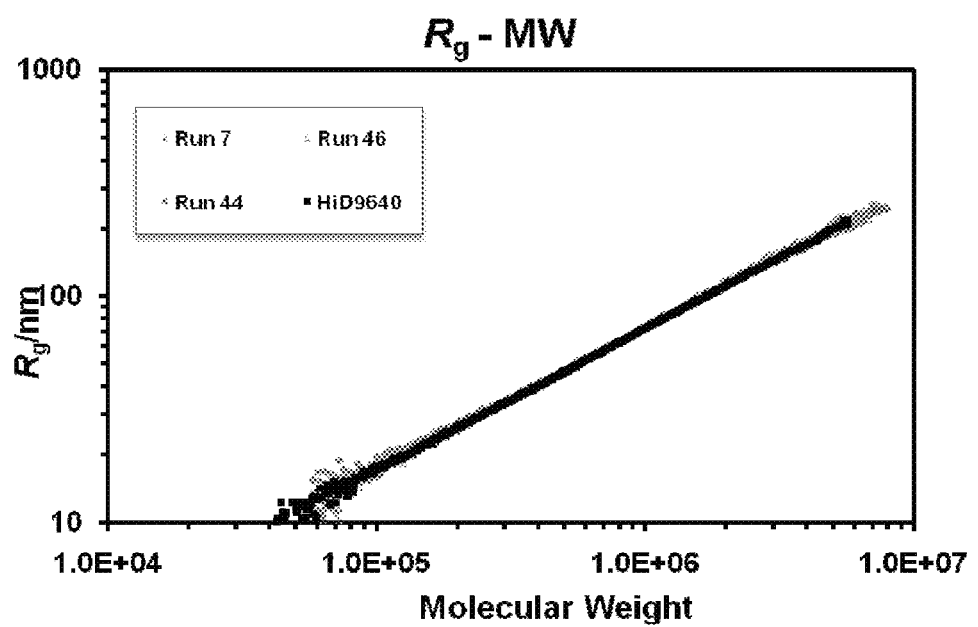
FIG. 2 is a plot of the radius of gyration as a function of molecular weight for the samples from Example 1.

The MWD of samples prepared using the different catalyst systems disclosed herein is presented in FIG. 1 while FIG. 2 provides a plot of the radius of gyration as a function of MW.

Example 2

Figure 3:
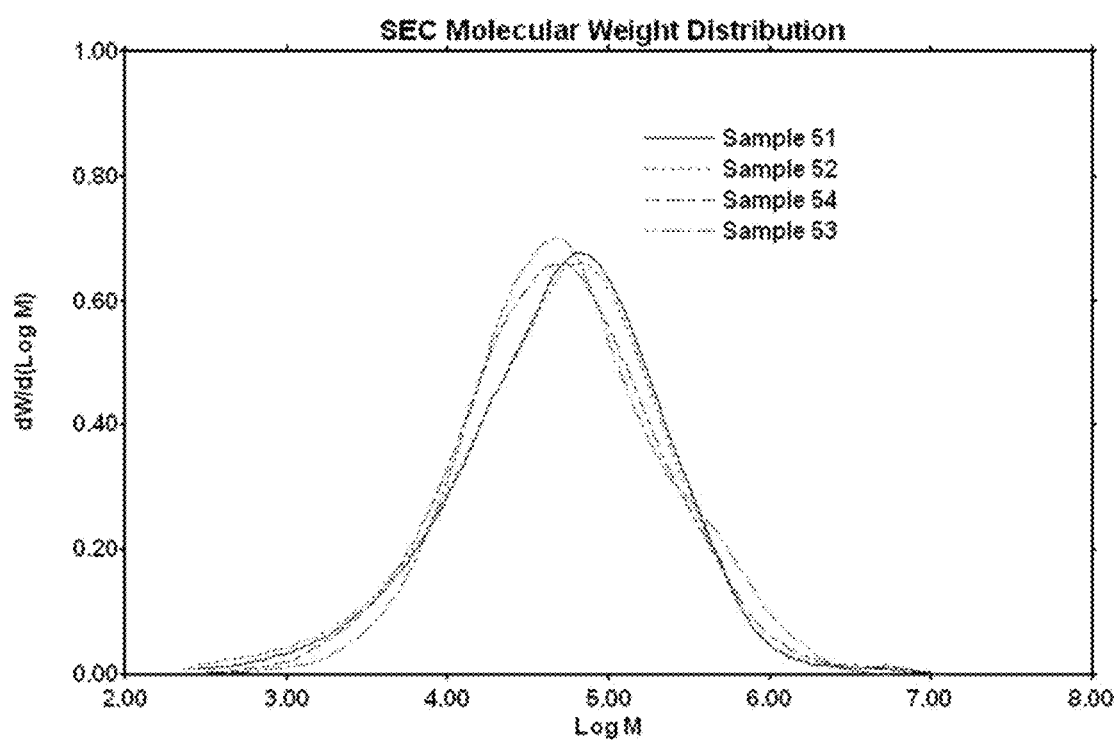
FIGS. 3 and 4 are graphs of the molecular weight distribution of polymer samples from Example 2.
Figure 4:
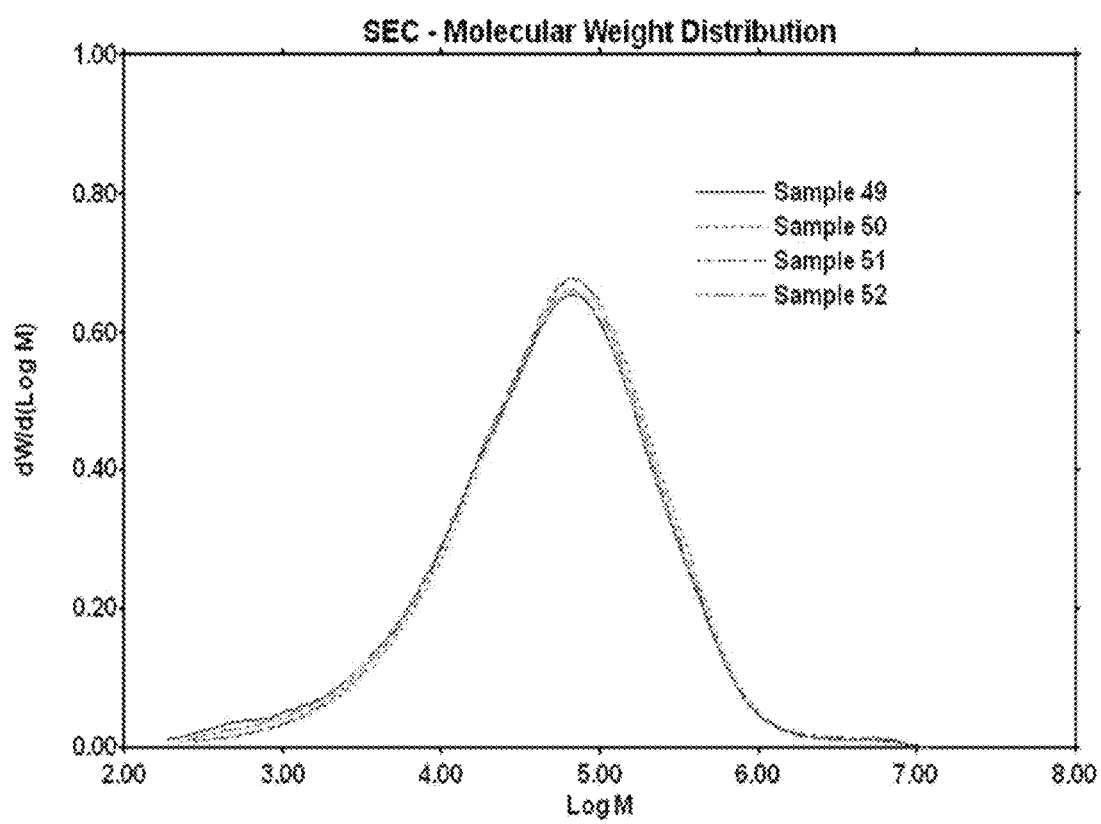

Resins produced using a catalyst system of the type described herein were obtained and tested for their film performance. Particularly, two sets of BIP samples comprising polyethylene were prepared and designated samples 49-52. Samples 49 and 50 were prepared as a first set of BIP samples while samples 51 and 52 were a second set of BIP samples that were prepared at a later date. Samples 53-59 comprised polyethylene resins prepared using dissimilar catalyst systems. Specifically, sample 53 was a commercial resin prepared using a Ziegler-Natta catalyst and having a melt index of 1; sample 54 was commercial resin prepared using a conventional chromium catalyst system and having a melt index of 1; sample 55 was a commercial unimodal resin prepared using a Ziegler Natta catalyst system and having a melt index of 2; samples 56 and 57 were commercial resins prepared using a modified chromium catalyst system and having a melt index of 2 and 1, respectively; sample 58 was a multimodal resin having an MI of 2.81 and comprised 60% of a low molecular weight (LMW) component having a MW=26 kg/mol and 40% of a high molecular weight (HMW) component having a MW=220 kg/mol; and sample 59 was a multimodal resin having a MI of 1.2 and comprised 40% of a LMW component having a MW=20 kg/mol and 60% of a HMW component having a MW=220 kg/mol which had been treated with peroxide to give a LCB value of 0.05 LCB/10,000 carbon atoms. GPC was conducted on samples 49-52 and a plot of these results is depicted in FIGS. 3 and 4. The results demonstrate embodiments of BIPs of the type disclosed herein that are unimodal compositions having a broad MWD. Additional results of GPC analysis of the 11 samples tested are presented in Table 3.

TABLE 3

| Sample No. | $M_n$ kg/mol | $M_w$ kg/mol | $M_z$ kg/mol | $M_w/M_n$ kg/mol | $M_z/M_w$ |
|---|---|---|---|---|---|
| 49 | 13 | 148 | 1357 | 11.4 | 9.2 |
| 50 | 15 | 154 | 1346 | 10.1 | 8.7 |
| 51 | 14 | 148 | 1482 | 10.7 | 10.0 |
| 52 | 11 | 154 | 1680 | 13.6 | 10.9 |
| 53 | 22 | 140 | 704 | 6.2 | 5.0 |
| 54 | 18 | 144 | 1083 | 8.0 | 7.5 |
| 55 | 18 | 115 | 437 | 6.3 | 3.8 |
| 56 | 15 | 135 | 1439 | 8.8 | 10.6 |
| 57 | 16 | 153 | 1470 | 9.5 | 9.6 |
| 58 | 15 | 107 | 345 | 7.2 | 3.2 |
| 59 | 11 | 114 | 294 | 10.0 | 2.6 |

The results demonstrate samples 49 to 52 had a molecular weight distribution in the range of those achieved with commercial chromium catalysts (samples 54, 56 and 58), implying that the ease of extrusion would be similar to that of these commercial products.

The rheological behavior of samples 49-59 was also assessed and those results are presented in Table 4.

TABLE 4

| Sample No. | $E_0$ Pa·s | $\tau_0$ s | a_0 | $E@_{100}$ Pa·s | Calculated LCB/10000C |
|---|---|---|---|---|---|
| 49 | 1.9E+04 | 0.020 | 0.2154 | 1.0E+03 | 0.029 |
| 50 | 1.9E+04 | 0.025 | 0.2368 | 1.2E+03 | 0.021 |
| 51 | 2.2E+04 | 0.017 | 0.1992 | 1.0E+03 | 0.032 |
| 52 | 5.1E+04 | 0.017 | 0.1541 | 1.0E+03 | 0.055 |
| 53 | 3.8E+04 | 0.182 | 0.2548 | 1.0E+03 | 0.066 |
| 54 | 9.5E+04 | 0.147 | 0.1649 | 9.0E+02 | 0.127 |
| 55 | 1.1E+04 | 0.030 | 0.2977 | 9.6E+02 | 0.053 |
| 56 | 3.5E+04 | 0.047 | 0.1769 | 7.1E+02 | 0.070 |
| 57 | 7.0E+04 | 0.110 | 0.1707 | 8.5E+02 | 0.069 |
| 58 | 3.3E+03 | 0.022 | 0.5442 | 8.1E+02 | 0.016 |
| 59 | 8.9E+03 | 0.023 | 0.4196 | 1.7E+03 | 0.0474 |

The results demonstrate embodiments of BIPs of the type described herein (i.e., Samples 49-52) that have higher zero shear viscosity without impacting too much the extrusion viscosity (Eta @ 100) over those of typical bimodal resins such as samples 58 and 59, suggesting better blown film bubble without an impact on output rates.

Barrier properties of the samples were also assessed and these results are presented in Table 5.

TABLE 5

| Sample No. | MI dg/min | Density g/cc | MVTR g·mil/100 in²/day 1 mil |
|---|---|---|---|
| 49 | 1.2 | 0.965 | 0.5 |
| 50 | 1.0 | 0.964 | 0.56 |
| 51 | 1.2 | 0.965 | 0.38 |
| 52 | 1.1 | 0.965 | 0.38 |
| 53 | 0.99 | 0.956 | 0.60 |
| 54 | 1.1 | 0.965 | 0.75 |
| 55 | 1.9 | 0.959 | 0.40 |
| 56 | 2.1 | 0.965 | 0.48 |
| 57 | 1.3 | 0.964 | 0.58 |
| 58 | 2.8 | 0.965 | 0.40 |
| 59 | 1.2 | 0.963 | 0.45 |

Figure 5:
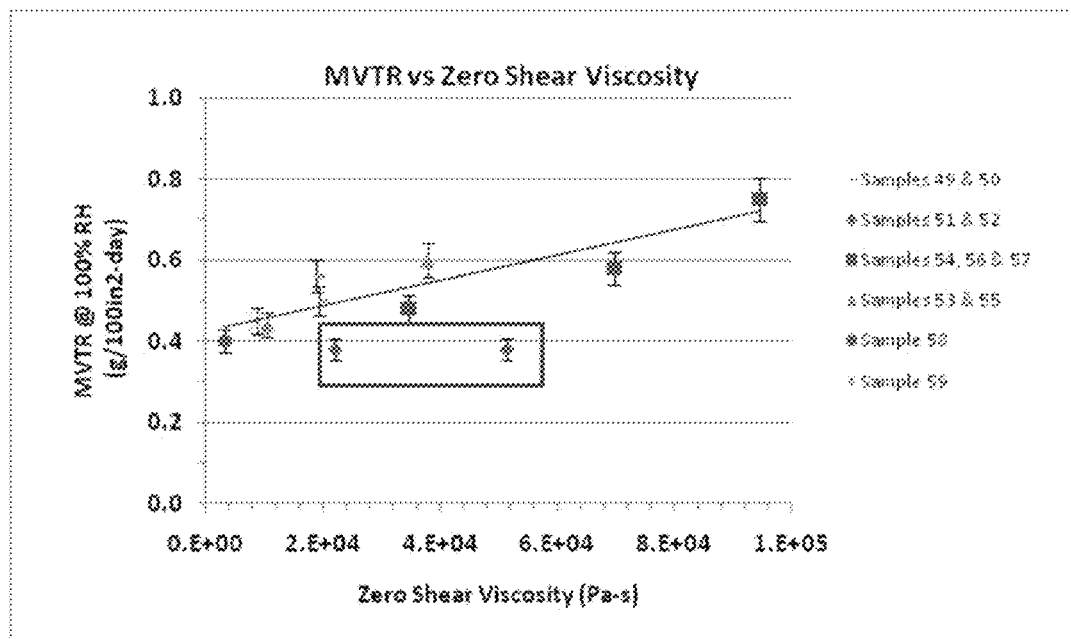
FIG. 5 is a plot of the moisture vapor transmission rate as a function of zero shear viscosity for the samples from Example 2.

The results demonstrate the homopolymer samples 51 and 52 achieved the lowest MVTR numbers at a melt index typical of a commercial application for a similar film gauge. Further a plot of the MVTR as a function of zero shear viscosity, FIG. 5, indicates that the samples would have a blown film bubble stability similar to some of the commercial resins while maintaining the MVTR advantage.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc., should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The discussion of a herein is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A compound of formula Cp'Cr(X)$_2$(L$_n$), wherein Cp' is $\eta^5$-C$_5$H$_4$CH$_2$CH$_2$CH=CH$_2$, X is a halide and L$_n$ is pyridine, THF or diethylether.
2. The compound of claim 1 wherein X is fluoride, chloride, bromide or iodide.
3. The compound of claim 1 wherein L$_n$ is pyridine.
4. The compound of claim 1 wherein L$_n$ is THF.
5. The compound of claim 1 wherein L$_n$ is diethyl ether.
6. The compound of claim 1 wherein X is chloride.
7. The compound of claim 3 wherein X is chloride.
8. The compound of claim 4 wherein X is chloride.
9. The compound of claim 5 wherein X is chloride.
10. The compound of claim 1 wherein X is fluoride.
11. The compound of claim 3 wherein X is fluoride.
12. The compound of claim 4 wherein X is fluoride.
13. The compound of claim 5 wherein X is fluoride.
14. A compound of formula Cp"Cr(X)$_2$(L$_n$), wherein Cp" is $\eta^5$-C$_5$H$_4$C(Me)$_2$CH$_2$CH$_2$CH=CH$_2$, X is a halide and L$_n$ is pyridine, THF or diethylether.
15. The compound of claim 14 wherein X is fluoride, chloride, bromide or iodide.
16. The compound of claim 14 wherein L$_n$ is pyridine.
17. The compound of claim 14 wherein L$_n$ is THF.
18. The compound of claim 14 wherein L$_n$ is diethyl ether.
19. The compound of claim 14 wherein X is chloride.
20. The compound of claim 16 wherein X is chloride.
21. The compound of claim 17 wherein X is chloride.
22. The compound of claim 18 wherein X is chloride.
23. The compound of claim 14 wherein X is fluoride.
24. The compound of claim 16 wherein X is fluoride.
25. The compound of claim 17 wherein X is fluoride.
26. The compound of claim 18 wherein X is fluoride.
27. $\eta^5$-C$_5$H$_4$CH$_2$CH$_2$CH=CH$_2$Cr(Cl)$_2$(THF).
28. $\eta^5$-C$_5$H$_4$C(Me)$_2$CH$_2$CH$_2$CH=CH$_2$Cr(Cl)$_2$(THF).

* * * * *